United States Patent
Silvestrini et al.

(10) Patent No.: US 8,167,939 B2
(45) Date of Patent: May 1, 2012

(54) OCULAR IMPLANT WITH STIFFNESS QUALITIES, METHODS OF IMPLANTATION AND SYSTEM

(75) Inventors: Thomas A. Silvestrini, Alamo, CA (US); Eugene de Juan, Jr., San Francisco, CA (US)

(73) Assignee: Transcend Medical, Inc., Menlo Park, CA (US)

( * ) Notice: Subject to any disclaimer, the term of this patent is extended or adjusted under 35 U.S.C. 154(b) by 0 days.

(21) Appl. No.: 13/245,802

(22) Filed: Sep. 26, 2011

(65) Prior Publication Data
US 2012/0016286 A1 Jan. 19, 2012

Related U.S. Application Data

(63) Continuation of application No. 12/694,691, filed on Jan. 27, 2010.

(60) Provisional application No. 61/147,988, filed on Jan. 28, 2009, provisional application No. 61/222,054, filed on Jun. 30, 2009, provisional application No. 61/246,017, filed on Sep. 25, 2009.

(51) Int. Cl.
*A61F 2/14* (2006.01)
(52) U.S. Cl. ...................... 623/6.12; 606/107
(58) Field of Classification Search .......... 606/107, 606/166; 623/4.1, 5.11–5.13, 6.12
See application file for complete search history.

(56) References Cited

U.S. PATENT DOCUMENTS

| | | | |
|---|---|---|---|
| 3,767,759 A | 10/1973 | Wichterle | |
| 3,788,327 A | 1/1974 | Donowitz | |
| 3,915,172 A | 10/1975 | Wichterle | |
| 4,037,604 A | 7/1977 | Newkirk | |
| 4,402,681 A | 9/1983 | Haas | |
| 4,457,757 A | 7/1984 | Molteno | |
| 4,521,210 A | 6/1985 | Wong | |
| 4,554,918 A | 11/1985 | White | |
| 4,604,087 A | 8/1986 | Joseph | |

(Continued)

FOREIGN PATENT DOCUMENTS
EP 0228185 7/1987
(Continued)

OTHER PUBLICATIONS

Barsky et al. "Evaluation of absorbable gelatin film (Gelfilm) in cyclodialysis clefts" Arch. Ophth. 60(6): 1044-1052,1958.

(Continued)

*Primary Examiner* — Ryan Severson
(74) *Attorney, Agent, or Firm* — Fred C. Hernandez; Mintz, Levin, Cohn, Ferris, Glovsky and Popeo, P.C.

(57) ABSTRACT

Described herein are devices and methods for treating eye conditions. Described is an ocular implant including an elongate member having an internal lumen forming a flow pathway, at least one inflow port communicating with the flow pathway, and at least one outflow port communicating with the flow pathway. The elongate member is adapted to be positioned in the eye such that at least one inflow port communicates with the anterior chamber, at least one outflow port communicates with the suprachoroidal space to provide a fluid pathway between the anterior chamber and the suprachoroidal space when the elongate member is implanted in the eye. The elongate member has a wall material imparting a stiffness to the elongate member. The stiffness is selected such that after implantation the elongate member deforms eye tissue surrounding the suprachoroidal space forming a tented volume.

26 Claims, 12 Drawing Sheets

U.S. PATENT DOCUMENTS

| | | |
|---|---|---|
| 4,634,418 A | 1/1987 | Binder |
| 4,722,724 A | 2/1988 | Schocket |
| 4,750,901 A | 6/1988 | Molteno |
| 4,787,885 A | 11/1988 | Binder |
| 4,826,478 A | 5/1989 | Schocket |
| 4,846,172 A | 7/1989 | Berlin |
| 4,863,457 A | 9/1989 | Lee |
| 4,886,488 A | 12/1989 | White |
| 4,900,300 A | 2/1990 | Lee |
| 4,946,436 A | 8/1990 | Smith |
| 4,968,296 A | 11/1990 | Ritch et al. |
| 5,041,081 A | 8/1991 | Odrich |
| 5,071,408 A | 12/1991 | Ahmed |
| 5,073,163 A | 12/1991 | Lippman |
| 5,092,837 A | 3/1992 | Ritch et al. |
| 5,127,901 A | 7/1992 | Odrich |
| 5,171,213 A | 12/1992 | Price, Jr. |
| 5,178,604 A | 1/1993 | Baerveldt et al. |
| 5,180,362 A | 1/1993 | Worst |
| 5,300,020 A | 4/1994 | L'Esperance, Jr. |
| 5,338,291 A | 8/1994 | Speckman et al. |
| 5,342,370 A | 8/1994 | Simon et al. |
| 5,346,464 A | 9/1994 | Camras |
| 5,370,607 A | 12/1994 | Memmen |
| 5,372,577 A | 12/1994 | Ungerleider |
| 5,397,300 A | 3/1995 | Baerveldt et al. |
| 5,433,701 A | 7/1995 | Rubinstein |
| 5,443,505 A | 8/1995 | Wong et al. |
| 5,454,746 A | 10/1995 | Guegan et al. |
| 5,476,445 A | 12/1995 | Baerveldt et al. |
| 5,558,629 A | 9/1996 | Baerveldt et al. |
| 5,558,630 A | 9/1996 | Fisher |
| 5,601,094 A | 2/1997 | Reiss |
| 5,626,558 A | 5/1997 | Suson |
| 5,626,559 A | 5/1997 | Solomon |
| 5,651,782 A | 7/1997 | Simon et al. |
| 5,676,944 A | 10/1997 | Alvarado et al. |
| 5,702,414 A | 12/1997 | Richter et al. |
| 5,704,907 A | 1/1998 | Nordquist et al. |
| 5,713,844 A | 2/1998 | Peyman |
| 5,741,292 A | 4/1998 | Mendius |
| 5,743,868 A | 4/1998 | Brown et al. |
| 5,752,928 A | 5/1998 | de Roulhac et al. |
| 5,807,302 A | 9/1998 | Wandel |
| 5,868,697 A | 2/1999 | Richter et al. |
| 5,882,327 A | 3/1999 | Jacob |
| 5,893,837 A | 4/1999 | Eagles et al. |
| 5,968,058 A | 10/1999 | Richter et al. |
| 6,007,510 A | 12/1999 | Nigam |
| 6,007,511 A | 12/1999 | Prywes |
| 6,019,786 A | 2/2000 | Thompson |
| 6,050,970 A | 4/2000 | Baerveldt |
| 6,077,299 A | 6/2000 | Adelberg et al. |
| 6,102,045 A | 8/2000 | Nordquist et al. |
| 6,142,969 A | 11/2000 | Nigam |
| 6,186,974 B1 | 2/2001 | Allan et al. |
| 6,203,513 B1 | 3/2001 | Yaron et al. |
| 6,221,078 B1 | 4/2001 | Bylsma |
| 6,251,090 B1 | 6/2001 | Avery et al. |
| 6,261,256 B1 | 7/2001 | Ahmed |
| 6,264,668 B1 | 7/2001 | Prywes |
| 6,468,283 B1 | 10/2001 | Richter et al. |
| 6,331,313 B1 | 12/2001 | Wong et al. |
| 6,375,642 B1 | 4/2002 | Grieshaber et al. |
| 6,383,219 B1 | 5/2002 | Telandro et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,471,777 B1 | 10/2002 | Kobayashi et al. |
| 6,508,779 B1 | 1/2003 | Suson |
| 6,510,600 B2 | 1/2003 | Yaron et al. |
| 6,524,275 B1 | 2/2003 | Lynch et al. |
| 6,533,768 B1 | 3/2003 | Hill |
| 6,537,568 B2 | 3/2003 | Olejnik et al. |
| 6,544,208 B2 | 4/2003 | Ethier et al. |
| 6,544,249 B1 | 4/2003 | Yu et al. |
| 6,558,342 B1 | 5/2003 | Yaron et al. |
| 6,589,203 B1 | 7/2003 | Mitrev |
| 6,595,945 B2 | 7/2003 | Brown |
| 6,626,858 B2 | 9/2003 | Lynch et al. |
| 6,638,239 B1 | 10/2003 | Bergheim et al. |
| 6,648,283 B2 | 11/2003 | Chase et al. |
| 6,666,841 B2 | 12/2003 | Gharib et al. |
| 6,676,607 B2 | 1/2004 | de Juan, Jr. et al. |
| 6,699,210 B2 | 3/2004 | Williams et al. |
| 6,699,211 B2 | 3/2004 | Savage |
| 6,719,750 B2 | 4/2004 | Varner et al. |
| 6,726,664 B2 | 4/2004 | Yaron et al. |
| 6,730,056 B1 | 4/2004 | Ghaem et al. |
| 6,736,791 B1 | 5/2004 | Tu et al. |
| 6,741,666 B1 | 5/2004 | Henry et al. |
| 6,780,164 B2 | 8/2004 | Bergheim et al. |
| 6,783,544 B2 | 8/2004 | Lynch et al. |
| 6,827,699 B2 | 12/2004 | Lynch |
| 6,827,700 B2 | 12/2004 | Lynch et al. |
| 6,881,197 B1 | 4/2005 | Nigam |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,966,888 B2 | 11/2005 | Cullen et al. |
| 6,969,384 B2 | 11/2005 | de Juan, Jr. et al. |
| 6,981,958 B1 | 1/2006 | Gharib et al. |
| 6,989,007 B2 | 1/2006 | Shadduck |
| 7,041,077 B2 | 5/2006 | Shields |
| 7,090,681 B2 | 8/2006 | Weber et al. |
| 7,094,225 B2 | 8/2006 | Tu et al. |
| 7,135,009 B2 | 11/2006 | Tu |
| 7,160,264 B2 | 1/2007 | Lisk, Jr. et al. |
| 7,163,543 B2 | 1/2007 | Smedley et al. |
| 7,186,232 B1 | 3/2007 | Smedley |
| 7,192,412 B1 | 3/2007 | Zhou et al. |
| 7,195,774 B2 | 3/2007 | Carvalho et al. |
| 7,207,965 B2 | 4/2007 | Simon |
| 7,220,238 B2 | 5/2007 | Lynch et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,431,710 B2 | 10/2008 | Tu et al. |
| 7,488,303 B1 | 2/2009 | Haffner et al. |
| 7,857,782 B2 | 12/2010 | Tu et al. |
| 2002/0013546 A1 | 1/2002 | Grieshaber et al. |
| 2002/0013572 A1 | 1/2002 | Berlin |
| 2002/0072673 A1 | 6/2002 | Yamamoto et al. |
| 2002/0111608 A1 | 8/2002 | Baerveldt et al. |
| 2002/0128613 A1 | 9/2002 | Nakayama |
| 2002/0133168 A1 | 9/2002 | Smedley et al. |
| 2002/0143284 A1 | 10/2002 | Tu et al. |
| 2002/0177856 A1 | 11/2002 | Richter et al. |
| 2002/0193725 A1 | 12/2002 | Odrich |
| 2003/0055372 A1 | 3/2003 | Lynch et al. |
| 2003/0060752 A1 | 3/2003 | Bergheim et al. |
| 2003/0097151 A1 | 5/2003 | Smedley et al. |
| 2003/0097171 A1 | 5/2003 | Elliott |
| 2003/0135149 A1 | 7/2003 | Cullen |
| 2003/0181848 A1 | 9/2003 | Bergheim et al. |
| 2003/0187384 A1 | 10/2003 | Bergheim et al. |
| 2003/0208163 A1 | 11/2003 | Yaron et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0088048 A1 | 5/2004 | Richter et al. |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0148022 A1 | 7/2004 | Eggleston |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu et al. |
| 2004/0225250 A1 | 11/2004 | Yablonski |
| 2004/0236343 A1 | 11/2004 | Taylor et al. |
| 2004/0249333 A1 | 12/2004 | Bergheim et al. |

| | | |
|---|---|---|
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260228 A1 | 12/2004 | Lynch et al. |
| 2005/0008673 A1 | 1/2005 | Snyder et al. |
| 2005/0049578 A1 | 3/2005 | Tu et al. |
| 2005/0090806 A1 | 4/2005 | Lynch et al. |
| 2005/0090807 A1 | 4/2005 | Lynch |
| 2005/0119601 A9 | 6/2005 | Lynch et al. |
| 2005/0119636 A1 | 6/2005 | Haffner et al. |
| 2005/0119737 A1 | 6/2005 | Bene |
| 2005/0125003 A1 | 6/2005 | Pinchuk et al. |
| 2005/0143817 A1 | 6/2005 | Hunter et al. |
| 2005/0149080 A1 | 7/2005 | Hunter et al. |
| 2005/0171507 A1 | 8/2005 | Christian et al. |
| 2005/0175663 A1 | 8/2005 | Hunter et al. |
| 2005/0181011 A1 | 8/2005 | Hunter et al. |
| 2005/0181977 A1 | 8/2005 | Hunter et al. |
| 2005/0182350 A1 | 8/2005 | Nigam |
| 2005/0191331 A1 | 9/2005 | Hunter et al. |
| 2005/0192527 A1 | 9/2005 | Gharib et al. |
| 2005/0197613 A1 | 9/2005 | Sniegowski et al. |
| 2005/0209549 A1 | 9/2005 | Bergheim et al. |
| 2005/0209550 A1 | 9/2005 | Bergheim et al. |
| 2005/0232972 A1 | 10/2005 | Odrich |
| 2005/0244462 A1 | 11/2005 | Farooq |
| 2005/0250788 A1 | 11/2005 | Tu et al. |
| 2005/0267397 A1 | 12/2005 | Bhalla |
| 2005/0267398 A1 | 12/2005 | Protopsaltis et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0283108 A1 | 12/2005 | Savage |
| 2005/0288617 A1 | 12/2005 | Yaron et al. |
| 2005/0288619 A1 | 12/2005 | Gharib et al. |
| 2006/0020248 A1 | 1/2006 | Prescott |
| 2006/0032507 A1 | 2/2006 | Tu et al. |
| 2006/0036207 A1 | 2/2006 | Koonmen et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0116626 A1 | 6/2006 | Smedley et al. |
| 2006/0155238 A1 | 7/2006 | Shields |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0235367 A1 | 10/2006 | Takashima et al. |
| 2006/0241580 A1 | 10/2006 | Mittelstein et al. |
| 2006/0241749 A1 | 10/2006 | Tu et al. |
| 2007/0010827 A1 | 1/2007 | Tu et al. |
| 2007/0088242 A1 | 4/2007 | Coroneo |
| 2007/0088432 A1 | 4/2007 | Solovay et al. |
| 2007/0106235 A1 | 5/2007 | Coroneo |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0149915 A1 | 6/2007 | Yablonski |
| 2007/0191863 A1* | 8/2007 | De Juan et al. ............... 606/108 |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2008/0015488 A1 | 1/2008 | Tu et al. |
| 2008/0045878 A1 | 2/2008 | Bergheim et al. |
| 2008/0058704 A1 | 3/2008 | Hee et al. |
| 2008/0147021 A1 | 6/2008 | Jani |
| 2008/0195027 A1 | 8/2008 | Coroneo |
| 2008/0200860 A1 | 8/2008 | Tu et al. |
| 2008/0228127 A1 | 9/2008 | Burns et al. |
| 2008/0234624 A2 | 9/2008 | Bergheim et al. |
| 2009/0036819 A1 | 2/2009 | Tu et al. |
| 2009/0182421 A1 | 7/2009 | Silvestrini |
| 2010/0010416 A1 | 1/2010 | De Juan, Jr. et al. |
| 2010/0134759 A1 | 6/2010 | Silvestrini |
| 2010/0137981 A1 | 6/2010 | Silvestrini et al. |
| 2010/0152641 A1 | 6/2010 | Yablonski |
| 2010/0274259 A1 | 10/2010 | Yaron et al. |
| 2011/0028883 A1 | 2/2011 | De Juan, Jr. et al. |
| 2011/0087148 A1 | 4/2011 | Silvestrini et al. |
| 2011/0098629 A1 | 4/2011 | De Juan, Jr. et al. |
| 2011/0112546 A1 | 5/2011 | De Juan, Jr. et al. |

FOREIGN PATENT DOCUMENTS

| | | |
|---|---|---|
| EP | 1184010 | 3/2002 |
| EP | 1310222 | 5/2003 |
| EP | 1473004 | 11/2004 |
| EP | 1477146 | 11/2004 |
| EP | 1977724 | 10/2008 |
| EP | 2027837 | 2/2009 |
| GB | 2101891 | 1/1983 |
| RU | 2018289 C1 | 8/1994 |
| RU | 2056818 C1 | 3/1996 |
| RU | 2074686 C1 | 3/1997 |
| RU | 2074687 C1 | 3/1997 |
| RU | 2157678 C1 | 10/2000 |
| WO | WO 89-00869 | 2/1989 |
| WO | WO 91-12046 | 8/1991 |
| WO | WO 92-19294 | 11/1992 |
| WO | WO 94-09721 | 5/1994 |
| WO | WO 94-09837 | 5/1994 |
| WO | WO 94-13234 | 6/1994 |
| WO | WO 95/08310 | 3/1995 |
| WO | WO 96-20742 | 7/1996 |
| WO | WO 96-36377 | 11/1996 |
| WO | WO 98-23237 | 6/1998 |
| WO | WO 98-30181 | 7/1998 |
| WO | WO 99-26567 | 6/1999 |
| WO | WO 00-64389 | 11/2000 |
| WO | WO 00-64390 | 11/2000 |
| WO | WO 00-64391 | 11/2000 |
| WO | WO 00-64393 | 11/2000 |
| WO | WO 00-64511 | 11/2000 |
| WO | WO 01-78631 | 10/2001 |
| WO | WO 01-78656 | 10/2001 |
| WO | WO 00-06223 | 11/2001 |
| WO | WO 01-97727 | 12/2001 |
| WO | WO 02-36052 | 5/2002 |
| WO | WO 02-070045 | 9/2002 |
| WO | WO 02-074052 | 9/2002 |
| WO | WO 02-080811 | 10/2002 |
| WO | WO 02-080829 | 10/2002 |
| WO | WO 02-087418 | 11/2002 |
| WO | WO 02-087479 | 11/2002 |
| WO | WO 02-089699 | 11/2002 |
| WO | WO 02-102274 | 12/2002 |
| WO | WO 03-015659 | 2/2003 |
| WO | WO 03-015667 | 2/2003 |
| WO | WO 03/041622 | 5/2003 |
| WO | WO 03-073968 | 9/2003 |
| WO | WO 03-099175 | 12/2003 |
| WO | WO 2004-014218 | 2/2004 |
| WO | WO 2004-026347 | 4/2004 |
| WO | WO 2004-043231 | 5/2004 |
| WO | WO 2004-056294 | 7/2004 |
| WO | WO 2004-060219 | 7/2004 |
| WO | WO 2004-062469 | 7/2004 |
| WO | WO 2004-110391 | 12/2004 |
| WO | WO 2005-016418 | 2/2005 |
| WO | WO 2005-046782 | 5/2005 |
| WO | WO 2005-055873 | 6/2005 |
| WO | WO 2005-105197 | 11/2005 |
| WO | WO 2005-107664 | 11/2005 |
| WO | WO 2005-107845 | 11/2005 |
| WO | WO 2006-012421 | 2/2006 |
| WO | WO 2006-036715 | 4/2006 |
| WO | WO 2007-087061 | 8/2007 |
| WO | WO 2007-115259 | 10/2007 |
| WO | WO 2007-130393 | 11/2007 |
| WO | WO 2008-061043 | 5/2008 |
| WO | WO 2009-012406 | 1/2009 |
| WO | WO 2009-158524 | 12/2009 |

OTHER PUBLICATIONS

Bick M.W., "Use of tantalum for ocular drainage" Arch Ophthal. Oct. 1949; 42(4): 373-88.

Bietti, G., "The present state of the use of plastics in eye surgery" Acta Ophthalmol (Copenh) 1955; 33(4):337-70.

Brown et al., "Internal Sclerectomy for Glaucoma Filtering Surgery with an Automated Trephine," Archives of Ophthalmology, vol. 105, Jan. 1987.

Burchfield JC, Kass MA, Wax MB. Primary valve malfunction of the Krupin eye valve with disk. J Glaucoma. Jun. 1997;6(3):152-6.

Chiou et al. "Ultrasound biomicroscopy of eyes undergoing deep sclerectomy with collagen implant" Br J Ophthalmol 80 (1996), pp. 541-544.

Chylack LT, Bellows AR. Molecular sieving in suprachoroidal fluid formation in man. Invest Ophthalmol Vis Sci 17: 420, 1978.

Classen et al., "A histopathologic and immunohistorchemical analysis of the filtration bleb after unsuccessful glaucoma seton implantation" Am. J. Ophthalmol. 122:205-12 (1996).

Cohen et al., "First day post-operative review following uncomplicated phacoemulsification" Eye 12(4):634-6 (1998).

Collaborative Normal-Tension Study Group. Comparison of glaucomatous progression between untreated patients with normal-tension glaucoma and patients with therapeutically reduced intraocular pressures. Am J Ophthalmol 1998;126:487-97.

Congdon N, O'Colmain B, Klaver CC, et al. Causes and prevalence of visual impairment among adults in the United States. Arch Ophthalmol 2004;122:477-85.

Demailly et al. "Non-penetrating deep sclerectomy (NPDS) with or without collagen device (CD) in primary open-angle glaucoma: middle-term retrospective study" International Ophthalmology 20: 131-140, 1997.

Derwent English abstract for EP 1184010, published Mar. 6, 2002 entitled: "Drainage unit for an eye, consists of a hollow line, a distribution member, and a pressure relief valve which only allows water to leave the eye chamber above a certain pressure," Accession Nbr. 12409716 [351].

Dinakaran et al., "Is the first post-operative day review necessary following uncomplicated phacoemulsification surgery?" Eye, 14(3A):364-6 (2000).

Draeger "Chirurgische Maβnahmen bei kongenitalem Glaukom" (Surgical Interventions in Congenital Glaucoma) Klin Monatsbl Augenheilkd 1993; 202(5): 425-427 [Article in German with English summary included].

Einmahl et al., "Evaluation of a novel biomaterial in the suprachoroidal space of the rabbit eye" Invest Ophthalmol Vis Sci. 43:1533-1539 (2002).

Ellis, RA "A Reduction Of Intraocular Pressure Using Plastics In Surgery" Am J Ophth. 50; 1960, 733-742.

Emi et al., "Hydrostatic pressure of the suprachoroidal space" Invest. Ophthal. Visual Sci. 30(2):233-238 (1989).

Fanous MM, Cohn RA. Propionibacterium endophthalmitis following Molteno tube repositioning. J Glaucoma. Aug. 1997;6(4):201-2.

Friedman DS, Wolfs RC, O'Colmain BJ, et al. Prevalence of open-angle glaucoma among adults in the United States. Arch Ophthalmol 2004;122:532-8.

Fuchs E., "Detachment of the choroid inadvertently during cataract surgery" [German] von Graefes Arch Ophthalmol, 51:199-224 (1900) [Article in German with English summary].

Gills et al., "Action of cyclodialysis utilizing an implant studied by manometry in a human eye" Expl Eye Res 1967; 6:75-78.

Gills, "Cyclodialysis Implants in Human Eyes" Am J Ophth 61:1966,841-846.

Gills JP, "Cyclodialysis implants" South Med J. 1967 60(7):692-5.

Goldberg "Management of Uncontrolled Glaucoma With the Molteno System" Australian and New Zealand Journal of Ophthalmology 1987; 15: 97-107.

Gordon MO, Kass. MA, for the Ocular Hypertension Treatment Study Group. The Ocular Hypertension Treatment Study. Design and baseline description of the participants. Arch Ophthalmol 1999:573-83.

Gross et al., "Surgical therapy of chronic glaucoma in aphakia and pseudophakia" Ophthalmology, 95:1195-201 (1988).

Harper SL, Foster CS. Intraocular lens explantation in uveitis. Int Ophthalmol Clin. 2000 Winter; 40(1):107-16.

Harrington "Cataract and Glaucoma. Management of the coexistent conditions and a description of a new operation combining lens extraction with reverse cyclodialysis." Am J Ophthalmol. May 1966;61(5 Pt 2):1134-40.

Heijl A, Leske MC, Bengtsson B, et al for the Early Manifest Glaucoma Trial Group. Reduction of intraocular pressure and glaucoma progression. Results from the Early Manifest Glaucoma Trial. Arch Ophthalmol 2002;120:1268-79.

Heine I., "Cyclodialysis, a new glaucoma operation" Dtsch Med Wochenschr, 31:824-826 (1905) [Article in German with English summary included].

Hildebrand et al., "Efficacy of anterior chamber decompression in controlling early intraocular pressure spikes after uneventful phacoemulsification" J. Catact Refract Surg., 29:1087-92 (2003).

Howorth DJ, "Feasibility study for a micromachined glaucoma drainage device" Cranfield University School of industrial and manufacturing science MSc Thesis Academic Year 2001-2002 Sep. 13, 2002.

Hylton et al., "Update on prostaglandin analogs" Curr Opin Ophthalmol, 14:65-9 (2003).

Javitt JC, Chiang YP. Preparing for managed competition. Utilization of ambulatory eye care visits to ophthalmologists. Arch Ophthalmol 1993;111:1034-5.

Jay JL, Allan D. The benefit of early trabeculectomy versus conventional management in primary open-angle glaucoma relative to severity of disease. Eye 1989; 3:528-35.

Jordan J., "A Novel Approach to Suprachoroidal Drainage for the Surgical Treatment of Intractable Glaucoma" J. Glaucoma 2006; 15:200-205.

Jordan JF, Dietlein TS, Dinslage S, Luke C, Konen W, Krieglstein GK. Cyclodialysis ab inferno as a surgical approach to intractable glaucoma. Graefes Arch Clin Exp Ophthalmol. Aug. 2007;245(8):1071-6.

Karlen, M. et al., "Deep sclerectomy with collagen implant: medium term results" Br. J. Ophthalmol, Jan. 1999, 83(1):6-11.

Kass MA, Heuer DK, Higginbotham EJ, et al for the Ocular Hypertension Treatment Study Group. The Ocular Hypertension Treatment Study. A randomized trial determines that topical ocular hypotensive medication delays or prevents the onset of primary open-angle glaucoma. Arch Ophthalmol 2002;120:701-13.

Klemm et al., "Experimental use of space-retaining substances with extended duration: functional and morphological results" Graefes Arch Clin Exp Ophthalmol Sep. 1995; 233(9):592-7.

Klemm et al. "Die Ultraschallbiomikroskopie als Kriterium der Funktionsprüufung des suprachorioidalen Spaltes nach kammerwinkelchirurgischen Eingriffen (Ultrasound Biomicroscopic Imaging for Assessment of the Suprachoroidal Cleft after Angle Surgery)" Klinische Monatsblätter für Augenheilkunde 1997; 210: 74-77 [Article in German with English summary included].

Kozlov et al., "Nonpenetrating deep sclerectomy with collagen" Eye microsurgery 3:44-46 (1990) [Article in Russian with English translation included].

Krejci, L., "Cyclodialysis with hydroxymethyl methacrylate capillary strip (HCS). Animal experiments with a new approach in glaucoma drainage surgery" Ophthalmologica 1972; 164(2):113-21.

Krejci L. "Microdrainage of anterior chamber of eye glaucoma operation using hydron capillary drain." Acta Univ Carol Med Monogr. 1974;(61):1-90.

Kupfer "Studies on intraocular pressure. I. A technique for polyethylene tube implantation into the anterior chamber of the rabbit." Arch Ophthalmol. Apr. 1961;65:565-70.

La Rocca "Gonioplasty in Glaucoma*A Preliminary Report" Br J Ophth 46:1962, 404-415.

Law et al., "Retinal Complications After Aqueous Shunt Surgical Procedures for Glaucoma" Arch Ophthal.; Dec. 1996; vol. 114:1473-1480.

Lee KY. Trabeculo-suprachoroidal shunt for treating recalcitrant and secondary glaucoma. Presented at the American Academy of Ophthalmology Annual Meeting, Anaheim, CA, 1991.

Lee et al., "Magnetic resonance imaging of the aqueous flow in eyes implanted with the trabeculo-suprachoroidal glaucoma seton" Invest. Ophthalmol. Vis. Sci. 33:948 (1992).

Leske MC, Heijl A, Hussein M, et al for the Early Manifest Glaucoma Trial Group. Factors for glaucoma progression and the effect of treatment. The Early Manifest Glaucoma Trial. Arch Ophthalmol 2003;121:48-56.

Lichter PR, Musch DC, Gillespie BW, et al and the CIGTS Study Group. Interim clinical outcomes in the Collaborative Initial Glaucoma Treatment Study comparing initial treatment randomized to medications or surgery. Ophthalmology 2001;108:1943-53.

Losche, W., "Proposals for improvement of cyclodialysis" Klin Monatsblatter Augenheilkd Augenarztl Fortbild 1952 121(6):715-6 [Article in German with English translation included].

Marx et al., "Use of the Ganciclovir Implant in the Treatment of Recurrent Cytomegalovirus Retinitis" Arch Ophthal.; Jul. 1996; vol. 114:815-820.

McPherson "Combined Trabeculotomy and Cataract Extraction as a Single Operation" Tr. Am. Ophth. Soc., vol. LXXIV, 1976; 251-260.

Migdal C, Gregory W, Hitchings R. Long term functional outcome after early surgery compared with laser and medicine in open-angle glaucoma. Ophthalmology 1994;101:1651-7.

Miglior S, Zeyen T, Pfeiffer N, et al for the European Glaucoma Prevention Study Group. The European Glaucoma Prevention Study design and baseline description of the participants. Ophthalmology 2002;109:1612-21.

Miglior S, Pfeiffer N, Zeyen T et al for the European Glaucoma Prevention Study Group. Results of the European Glaucoma Prevention Study. Ophthalmology 2005;112:366-75.

Miki, MD et al., "Intraocular Cannula for Continuous, Chronic Drug Delivery-Histopathic Observations and Function" Arch Ophthal.; May 1985; vol. 103:712-717.

Molteno et al. "Long tube implants in the management of glaucoma" South African Medical Journal, Jun. 26, 1976;50(27):1062-6.

Molteno et al. "The Vicryl tie technique for inserting a draining implant in the treatment of secondary glaucoma." Australian and New Zealand Journal of Ophthalmology 1986; 14: 343-354.

Moses RA "Detachment of ciliary body-anatomical and physical considerations" Investigative Ophthalmology & Visual Science, Assoc. For Research In Vision and Ophthalmology, US, vol. 4, No. 5, Oct. 1, 1965.

Nesterov, AP, et al., "Surgical stimulation of the uveoscleral outflow. Experimental studies on enucleated human eyes" Acta Opthalmol (Copenh) June; 57(3):409-17 (1979).

Nguyen et al., "Complications of Baerveldt Glaucoma Drainage Implants" Arch Ophthal.; May 1998; vol. 116:571-575.

Noecker RJ. Clinical Evaluation of a Novel Gold Micro-Shunt for Reduction of 10 P in Refractory Glaucomas. American Glaucoma Society Annual Meeting, San Francisco, CA,2007.http://www.glaucomaweb.org/associations/5224/files/AGS%20AM07%20Prgrm%20FIN_AL.pdf. Accessed Nov. 1, 2008).

O'Brien et al. "Cyclodialysis" Arch Ophthal. 1949;42(5):606-619.

Ozdamar, A., et al., "Suprachoroidal seton implantation in refractory glaucoma: a novel surgical technique" J. Glaucoma Aug. 2003; 12(4):354-9.

Pinnas, G. et al. "Cyclodialysis with teflon tube implants" Am J. Ophthalmol Nov. 1969; 68(5):879-883.

Portney GL, "Silicone elastomer implantation cyclodialysis." Arch Ophthalmol 1973; 89: 10-12.

Primary Open Angle Glaucoma. Preferred Practice Patterns, American Academy of Ophthalmology.http://one.aao.org/CE/PracticeGuidelines/PPP_Content.aspx?cid=a5a59e02-450b-4d50-8091-b2dd2lefl ff2#references (Accessed Nov. 1, 2008).

Pruett et al., "The Fishmouth Phenomenon-II. Wedge Scleral Buckling" Arch Ophthal.; Oct. 1977; vol. 95:1782-1787.

Qadeer "Acrylic Gonio-Subconjunctival Plates in Glaucoma Surgery" Br J Ophthalmol. Jun. 1954; 38(6): 353-356.

Quigley HA, Vitale S. Models of open-angle glaucoma prevalence and incidence in the United States. Invest Ophthalmol Vis Sci 1997; 38:83-91.

Richards et al. "Artificial Drainage Tubes for Glaucoma" Am J Ophth 60:1965,405-408.

Ritch R, Shields MB, Krupin T. The Glaucomas. St. Louis: Mosby, 1996; 337-343).

Rosenberg, L., et al. "Implants in glaucoma surgery" Chapter 88, The Glaucomas, Ritch et al. Eds. 2nd Ed. Mosby St. Louis 1986; p. 1783-1807.

Row, H., "Operation to control glaucoma: preliminary report"(1934) Arch. Ophthal 12:325.

Sampimon "A New Approach to Filtering Glaucoma Surgery" Ophthalmologica (Basel) 151: 1966, 637-644.

Schappert S. Office visits for glaucoma: United States, 1991-92. Advance data from vital and health statistics. vol. 262. Hyattsville, MD: National Center for Health Statistics, 1995.

Shaffer RN, Weiss DI. Concerning cyclodialysis and hypotony. Arch Ophthalmol 68: 25, 1962.

Solx Clinical Literature Handout; Industry Show Feb. 2006; "The SOLX Gold Micro-shunt (GMS) treatment".

Sommer A, Tielsch JM, Katz J, et al. Racial differences in the cause-specific prevalence of blindness in east Baltimore. N Engl J Med 1991;325:1412-7.

Sourdille et al. "Reticulated hyaluronic acid implant in non-perforating trabecular surgery." J Cataract Refract Surg 25: 332-339. (1999).

Srinivasan, R., et al., "Microbial contamination of the anterior chamber during phacoemulsification" J. Cataract Refract Surg. 28:2173-6 (2002).

Suguro K, Toris CB, Pederson JE. Uveoscleral outflow following cyclodialysis in the monkey eye using a fluorescent tracer. Invest Ophthalmol Vis Sci 1985: 26, 810.

The Advanced Glaucoma Intervention Study (AGIS): 7. The relationship between control of intraocular pressure and visual field deterioration. The AGIS Investigators. Am J Ophthalmol 2000;130:429-40.

The Advanced Glaucoma Intervention Study (AGIS); 13. Comparison of treatment outcomes within race: 10-year results. Ophthalmology 2004;111:651-64.

The Glaucoma Laser Trial (GLT). 2. Results of argon laser trabeculoplasty versus topical medicines. The Glaucoma Laser Trial Research Group. Ophthalmology 1990;97:1403-13.

The Glaucoma Laser Trial (GLT) and Glaucoma Laser Trial Follow-up Study: 7. Results. Am J Ophthahnol 1995;120:718-31.

Thiagalingam S, Tarongoy P, Hamrah P, Lobo AM, Nagao K, Barsam C, Bellows R, Pineda R. Complications of cosmetic iris implants. J Cataract Refract Surg. Jul. 2008;34(7):1222-4.

Tielsch JM, Sommer A, Katz J, et al. Racial variations in the prevalence of primary open-angle glaucoma. The Baltimore Eye Survey. JAMA 1991;266:369-74.

Toris et al. "Effect of intraocular pressure on uveoscleral outflow following cyclodialysis in the monkey eye." Investigative Ophthalmology & Visual Science. 26 (1985) 1745-1749.

Toris CB. Extravascular albumin concentration of the uvea. Invest Ophthalmol Vis Sci 1990; 31:43.

Toris, C., et al., "Aqueous humor dynamics in the aging human eye" Am J. Ophthalmol., 127:407-12 (1999).

Trigler L, Proia AD, Freedman SF. Fibrovascular ingrowth as a cause of Ahmed glaucoma valve failure in children. Am J Ophthalmol. Feb. 2006;141(2):388-9.

Troncosco, U.M., "Cyclodialysis with insertion of metal implant in treatment of glaucoma Preliminary report" Arch. Ophthal. 23:270 (1940).

Veen et al. "The gonioseton, a surgical treatment for chronic glaucoma" Documenta Ophthalmologica vol. 75, Nos. 3-4, 365-375. (1990).

Vossmerbaeumer U, Ditzen K, Jonas JB. Removal of an intracorneal hydrogel implant for hyperopia after Lasik. J Refract Surg. Jan. 2007;23(1):102-4.

Wamsley S, Moster MR, Rai S, Alvim HS, Fontanarosa J. Results of the use of the Ex-PRESS miniature glaucoma implant in technically challenging, advanced glaucoma cases: a clinical pilot study. Am J Ophthalmol. Dec. 2004; 138(6):1049-51.

Yablonski, M., "Some thoughts on the pressure dependence of uveoscleral flow" Journal of Glaucoma, 12(1):90-92 (2003).

Yablonski, "Trabeculectomy with Internal Tube Shunt: a novel glaucoma surgery" J. Glaucoma 14:91-97 (2005).

Yoo C, Kwon SW, Kim YY. Pericardium plug in the repair of the corneoscleral fistula after ahmed glaucoma valve explantation. Korean J Ophthalmol. Dec. 2008;22 (4):268-71.

Zhou, J., et al., "A trabecular bypass flow hypothesis" J Glaucoma. 14(1):74-83 (2005).

Grant, W.M., MD, Further Studies on Facility of Flow Through the Trabecular Meshwork, A.M.A. Archives of Ophthalmololgy, Oct. 1958, vol. 60, pp. 523-533.

Hoskins, et al., "Aqueous Humor Outflow", Becker-Shaffer's Diagnosis and Therapy of the Glaucomas, 6th Edition, Chapter 4, pp. 41-66, 1989.

Olsen, Timothy W., et al., Cannulation of the Suprachoroidal Space: A Novel Drug Delivery Methodology to the Posterior Segment, American Journal of Ophthalmology, vol. 142, No. 5, Nov. 2006, pp. 777-787.e2.

Rohen, Johannes W., Anatomy of the Aqueous Outflow Channels, Glaucoma, vol. 1, Chapter 14, pp. 277-296, Edited by J.E. Cairns, Grune & Stratton, Harcourt Brace Jovanovich Publishers, 1986.

Rowan, Patrick J., MD, Combined Cyclodialysis and Cataract Surgery, Ophthalmic Surgery and Lasers, Dec. 1998, vol. 29, No. 12, pp. 962-968 (9 pages).

Troncoso, Manuel U., Tantalum implants for inducing hypotny, Am Journal of Ophthalmology, vol. 32(4):499-508 (1949).

Wagner, Justin A., et al., Characterization of Uveoscleral Outflow in Enucleated Porcine Eyes Perfused under Constant Pressure, Invest Ophthalmol Vis Sci., Published in edited form in Sep. 2004, vol. 45, Issue 9, pp. 3203-3206.

\* cited by examiner

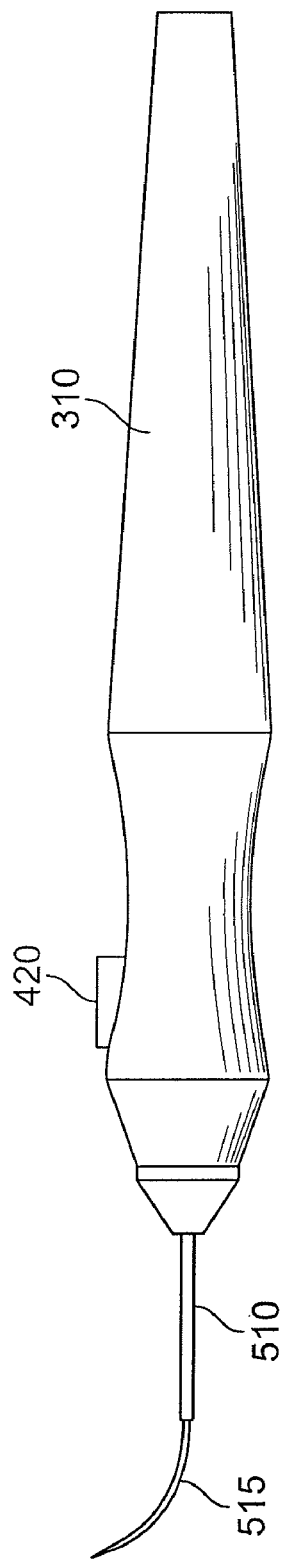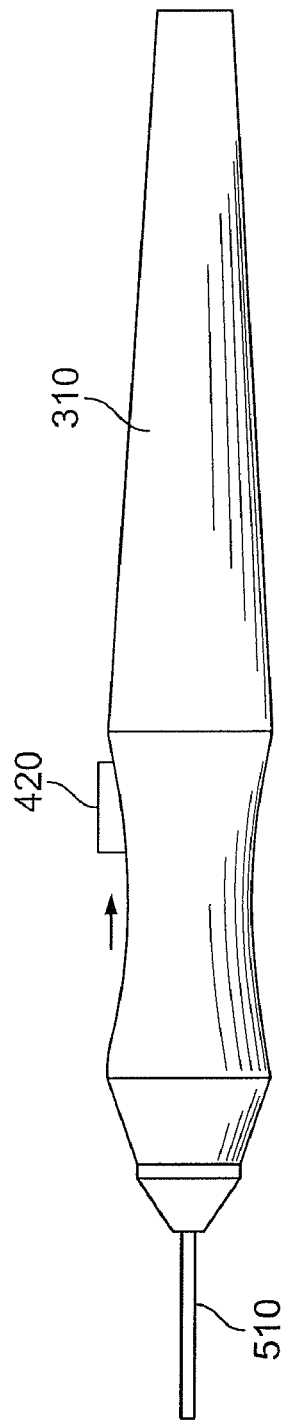
FIG. 5C
FIG. 5D

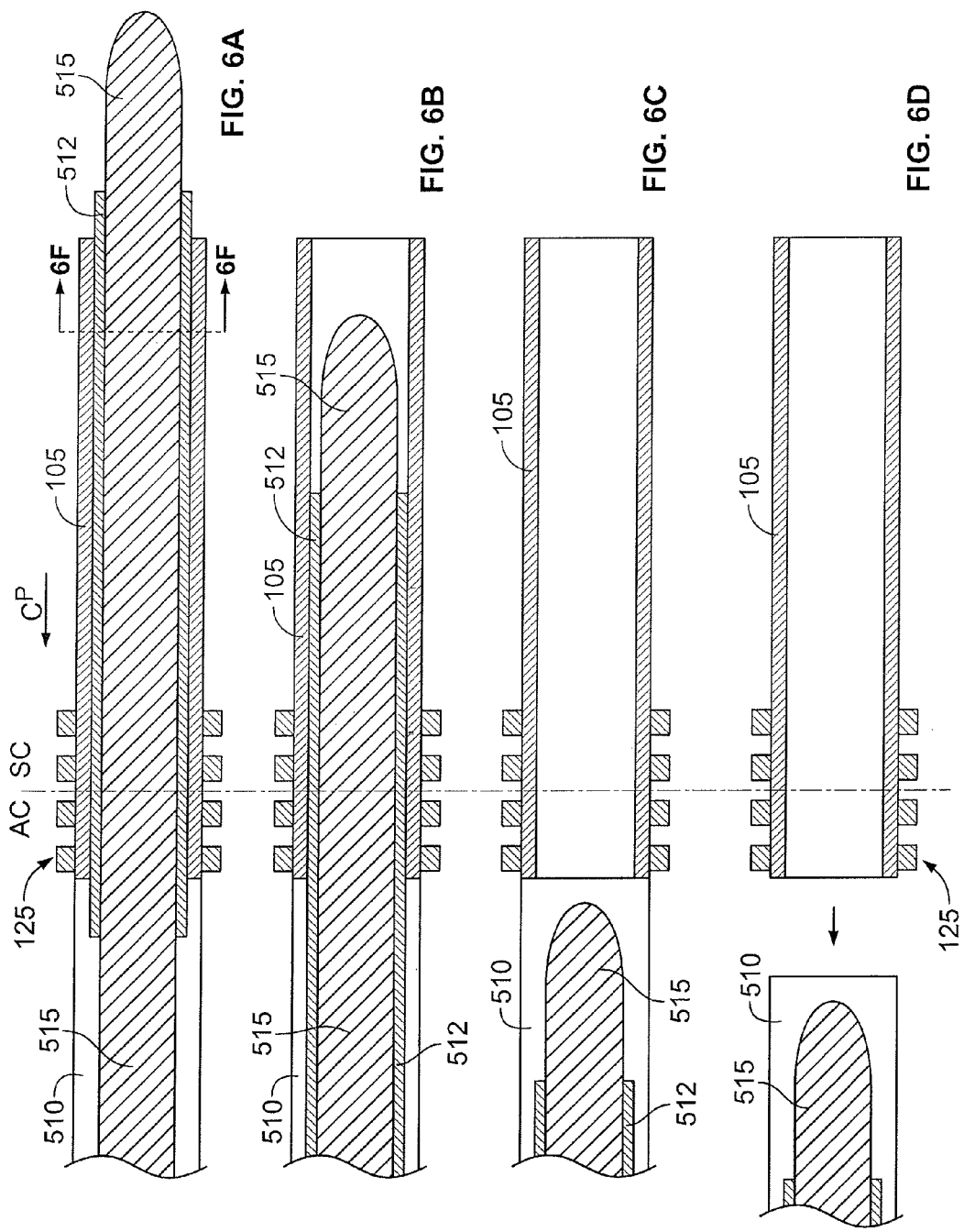

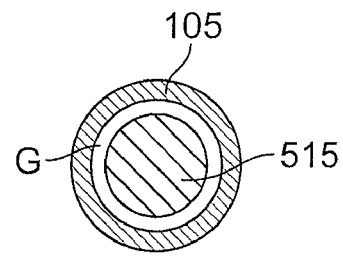
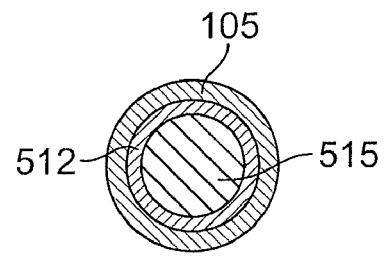
FIG. 6E       FIG. 6F
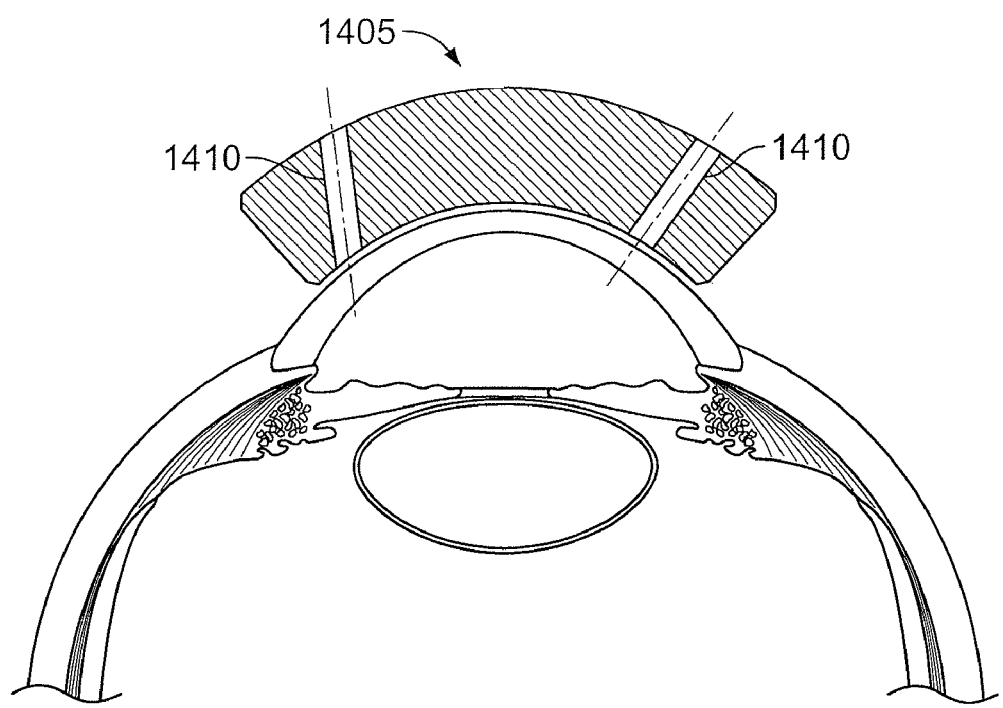
FIG. 6G

OCULAR IMPLANT WITH STIFFNESS QUALITIES, METHODS OF IMPLANTATION AND SYSTEM

REFERENCE TO PRIORITY DOCUMENTS

This application is a continuation of co-pending U.S. patent application Ser. No. 12/694,691, filed Jan. 27, 2010, entitled "Ocular Implant with Stiffness Qualities, Methods of Implantation and System", which claims priority benefit under 35 U.S.C. 119(e) of U.S. Provisional Patent Application Ser. Nos. 61/147,988, filed Jan. 28, 2009, entitled "Ocular Implant with Stiffness Qualities," 61/222,054, filed Jun. 30, 2009, entitled "Ocular Device Implantation Method and System," and 61/246,017, filed Sep. 25, 2009, entitled "Ocular Implant to Reduce Aqueous Humor Production." The filing dates and disclosures of the Patent Applications are hereby incorporated by reference in their entirety.

BACKGROUND

This disclosure relates generally to methods and devices for use in treating glaucoma. In particular, this disclosure relates to a device that is implantable in the eye to form a fluid passageway between the anterior chamber and the suprachoroidal space wherein the device has a relative stiffness that causes a portion of the suprachoroidal space to achieve desired shape when the implant is deployed. The implants described herein can also affect the production of aqueous humor by the ciliary body.

The mechanisms that cause glaucoma are not completely known. It is known that glaucoma results in abnormally high pressure in the eye, which leads to optic nerve damage. Over time, the increased pressure can cause damage to the optic nerve, which can lead to blindness. Treatment strategies have focused on keeping the intraocular pressure down in order to preserve as much vision as possible over the remainder of the patient's life.

Past treatment includes the use of drugs that lower intraocular pressure through various mechanisms. The glaucoma drug market is an approximate two billion dollar market. The large market is mostly due to the fact that there are not any effective surgical alternatives that are long lasting and complication-free. Unfortunately, drug treatments as well as surgical treatments that are available need much improvement, as they can cause adverse side effects and often fail to adequately control intraocular pressure. Moreover, patients are often lackadaisical in following proper drug treatment regimens, resulting in a lack of compliance and further symptom progression.

With respect to surgical procedures, one way to treat glaucoma is to implant a drainage device in the eye. The drainage device functions to drain aqueous humor from the anterior chamber and thereby reduce the intraocular pressure. The drainage device is typically implanted using an invasive surgical procedure. Pursuant to one such procedure, a flap is surgically formed in the sclera. The flap is folded back to form a small cavity and the drainage device is inserted into the eye through the flap. Such a procedure can be quite traumatic as the implants are large and can result in various adverse events such as infections and scarring, leading to the need to re-operate.

Current devices and procedures for treating glaucoma have disadvantages and only moderate success rates. The procedures are very traumatic to the eye and also require highly accurate surgical skills, such as to properly place the drainage device in a proper location. In addition, the devices that drain fluid from the anterior chamber to a subconjunctival bleb beneath a scleral flap are prone to infection, and can occlude and cease working. This can require re-operation to remove the device and place another one, or can result in further surgeries. In view of the foregoing, there is a need for improved devices and methods for the treatment of glaucoma.

SUMMARY

There is a need for improved devices and methods for the treatment of eye diseases such as glaucoma. In particular, there is a need for simplified, low profile devices for the treatment of glaucoma and other diseases using a delivery system that uses a minimally-invasive procedure.

In an embodiment described herein is an ocular implant including an elongate member having an internal lumen forming a flow pathway, at least one inflow port communicating with the flow pathway, and at least one outflow port communicating with the flow pathway. The elongate member is adapted to be positioned in the eye such that at least one inflow port communicates with the anterior chamber, at least one outflow port communicates with the suprachoroidal space to provide a fluid pathway between the anterior chamber and the suprachoroidal space when the elongate member is implanted in the eye. The elongate member has a wall material imparting a stiffness to the elongate member. The stiffness is selected such that after implantation the elongate member deforms eye tissue surrounding the suprachoroidal space forming a tented volume.

The stiffness of the elongate member can be greater than a stiffness of the eye tissue surrounding the suprachoroidal space. The elongate member can form a chord relative to a curvature of the suprachoroidal space. The eye tissue surrounding the suprachoroidal space can include an outer tissue shell having a first boundary and a first curvature and an inner tissue shell having a second boundary and a second curvature, wherein the first curvature and the second curvature form a ratio. The stiffness of the elongate member can change the ratio between the first curvature and the second curvature. The elongate member can be curved such that it intersects, but does not conform to the first or second curvatures when implanted.

The wall material can have a Young's modulus that is less than 30,000 pounds per square inch. The wall material can have a Young's modulus that is between about 30,000 pounds per square inch and 70,000 pounds per square inch. The wall material can have a Young's modulus that is approximately 200,000 pounds per square inch. The wall material can have a Young's modulus that is less than or equal to 40,000,000 pounds per square inch. The elongate member can have an inner diameter of about 0.012 inch and an outer diameter of about 0.015 inch. The elongate member can have a length in the range of about 0.250 inch to about 0.300 inch.

Also disclosed are methods of implanting an ocular device into the eye. In an embodiment, the method includes forming an incision in the cornea of the eye; loading onto a delivery device an implant having a fluid passageway and a wall material imparting a stiffness to the implant; inserting the implant loaded on the delivery device through the incision into the anterior chamber of the eye; passing the implant along a pathway from the anterior chamber into the suprachoroidal space; positioning at least a portion of the implant in the suprachoroidal space such that a first portion of the fluid passageway communicates with the anterior chamber and a second portion of the fluid passageway communicates with the suprachoroidal space to provide a fluid passageway between the suprachoroidal space and the anterior chamber;

and releasing the implant from the delivery device such that the implant achieves a predetermined shape within the suprachoroidal space and forms a chord relative to a curvature of the suprachoroidal space. The chord can be straight or the chord can be curved. The stiffness of the implant can be greater than a stiffness of adjacent eye tissue.

In another embodiment the method of treating an eye includes forming an incision in the cornea of the eye; inserting an implant through the incision into the anterior chamber of the eye wherein the implant includes a fluid passageway; passing the implant along a pathway from the anterior chamber into the suprachoroidal space; positioning the implant such that a first portion of the fluid passageway communicates with the anterior chamber and a second portion of the fluid passageway communicates with the suprachoroidal space to provide a fluid passageway between the suprachoroidal space and the anterior chamber; and applying a force on the ciliary body with the implant so as to reduce aqueous outflow from the ciliary body.

Applying a force on the ciliary body with the implant can elicit an increase in prostaglandin production by the ciliary body. Applying a force on the ciliary body with the implant can include displacing at least a portion of the ciliary body. Applying a force on the ciliary body with the implant does not necessarily displace the ciliary body.

Other features and advantages should be apparent from the following description of various embodiments, which illustrate, by way of example, the principles of the invention.

BRIEF DESCRIPTION OF THE DRAWINGS

FIGS. 5C and 5D show the delivery system of FIG. 5B during actuation;

FIG. 6A-6D show an exemplary mechanism for delivering an implant;

FIG. 6E is a cross-sectional view of an embodiment of a delivery system;

FIG. 6F is a cross-sectional view of the delivery system of FIG. 6A taken along line F-F;

FIG. 6G shows a cross-sectional view of the eye and a viewing lens;

It should be appreciated that the drawings herein are exemplary only and are not meant to be to scale.

DETAILED DESCRIPTION

There is a need for improved methods and devices for the treatment of eye diseases. Disclosed herein are low profile, simplified devices that can be used in the eye for the treatment of glaucoma and other eye diseases. The devices can be placed in the eye such that the implant provides a fluid pathway for the flow or drainage of aqueous humor from the anterior chamber to the suprachoroidal space. The devices described herein are designed to enhance aqueous flow through the normal outflow system of the eye with minimal to no complications.

There is also a need for low profile, simplified delivery devices to deliver an implant that can gently and bluntly dissect between tissue margins or tissue layer boundaries, for example, between the iris root and the scleral spur or the iris root part of the ciliary body and the scleral spur into the supraciliary space and then, further on, between the sclera and the choroid into the suprachoroidal space in the eye. The devices described herein can be implanted in the eye using a delivery system that uses a minimally-invasive procedure and can penetrate certain tissues and separate tissue boundaries while avoid penetrating certain other tissues. Any of the procedures and devices described herein can be performed in conjunction with other therapeutic procedures, such as laser iridotomy, laser iridoplasty, and goniosynechialysis (a cyclodialysis procedure).

Described herein also are devices, systems and methods for the treatment of eye diseases such as glaucoma that cause a reduction in aqueous humor production. Aqueous humor is generally produced by ciliary body cells. Implanting a device that can impose a force such as a radial force on structures in the eye such as the ciliary body aqueous humor production by these cells can be reduced resulting in a decrease in intraocular pressure.

Figure 1:
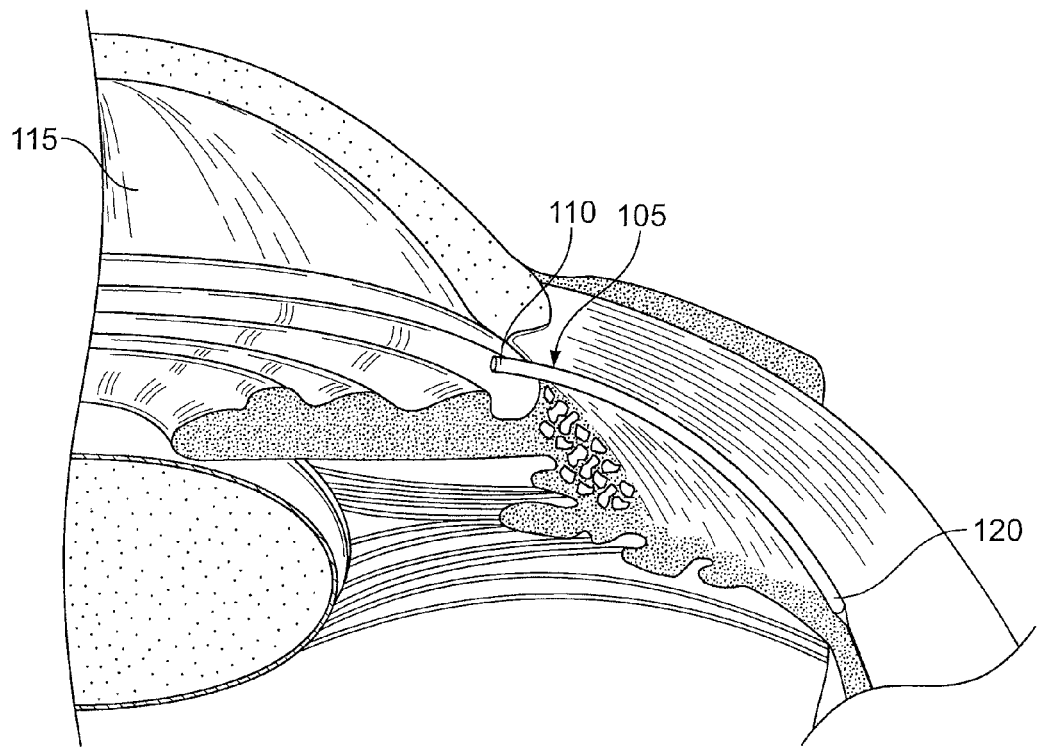
FIG. 1 is a cross-sectional, perspective view of a portion of the eye showing the anterior and posterior chambers of the eye.

FIG. 1 is a cross-sectional, perspective view of a portion of the eye showing the anterior and posterior chambers of the eye. A schematic representation of an implant 105 is positioned inside the eye such that a proximal end 110 is located in the anterior chamber 115 and a distal end 120 extends to a region of the eye that is between the ciliary body and the sclera. Alternatively, the distal end 120 can extend to a region of the eye that is posterior to the ciliary body, such as between the choroid and the sclera. The suprachoroidal space (sometimes referred to as the perichoroidal space) can include the region between the sclera and the choroid. The suprachoroidal space can also include the region between the sclera and the ciliary body. In this regard, the region of the suprachoroidal space between the sclera and the ciliary body may sometimes be referred to as the supraciliary space. The implant described herein is not necessarily positioned between the choroid and the sclera. The implant 105 can be positioned at least partially between the ciliary body and the sclera or it can be at least partially positioned between the sclera and the choroid. In any event, the implant 105 can provide a fluid pathway for flow of aqueous humor through or along the implant between the anterior chamber and the suprachoroidal space.

In an embodiment, the implant 105 can be an elongate element having one or more internal lumens through which aqueous humor can flow from the anterior chamber 115 into the suprachoroidal space. The implant 105 can have a substantially uniform diameter along its entire length, although the shape of the implant 105 can vary along its length (either before or after insertion of the implant), as described below. Moreover, the implant 105 can have various cross-sectional shapes (such as circular, oval or rectangular shape) and can vary in cross-sectional shape moving along its length. The cross-sectional shape can be selected to facilitate easy insertion into the eye. The following applications describe exemplary implants and are incorporated by reference in their entirety: U.S. Patent Publication Nos. 2007-0191863 and 2009-0182421.

At least a portion of the implant can be formed of a structure having a stiffness that causes the implant 105 to form a chord (either straight, curved, or curvilinear) relative to the natural-state curvature of the suprachoroidal space, as described in detail below. That is, the implant can define a line that intersects at least two points along a curve that conforms to the natural curvature of the suprachoroidal space if the implant were not present. The implant 105 can have a stiffness that is greater than the stiffness of adjacent eye tissue (e.g., the choroid and the sclera or the ciliary body and sclera) such that the implant 105 deforms the eye tissue and forms a chord relative to the curvature of the suprachoroidal space when implanted in the eye. The presence of the implant 105 can cause the suprachoroidal space to achieve a geometry that produces a tented volume within the suprachoroidal space.

Eye Anatomy and Glaucoma

Figure 2:
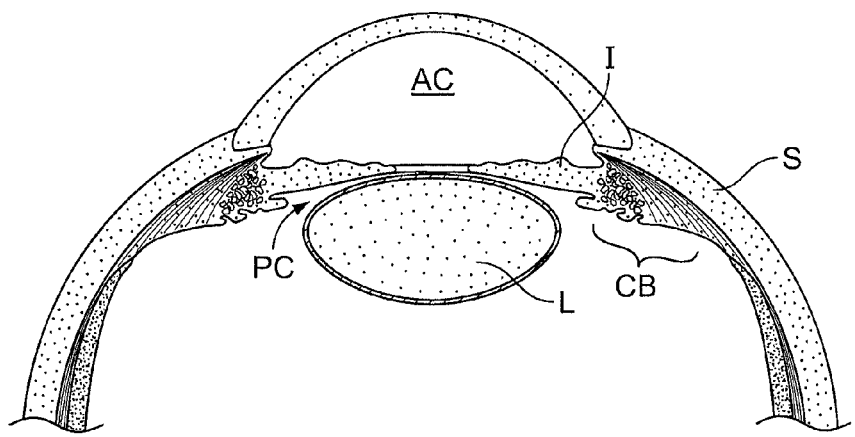
FIG. 2 is a cross-sectional view of a human eye.

FIG. 2 is a cross-sectional view of a portion of the human eye. The eye is generally spherical and is covered on the outside by the sclera S. The retina lines the inside posterior half of the eye. The retina registers the light and sends signals to the brain via the optic nerve. The bulk of the eye is filled and supported by the vitreous body, a clear, jelly-like substance. The elastic lens L is located near the front of the eye. The lens L provides adjustment of focus and is suspended within a capsular bag from the ciliary body CB, which contains the muscles that change the focal length of the lens. A volume in front of the lens L is divided into two by the iris I, which controls the aperture of the lens and the amount of light striking the retina. The pupil is a hole in the center of the iris I through which light passes. The volume between the iris I and the lens L is the posterior chamber PC. The volume between the iris I and the cornea is the anterior chamber AC. Both chambers are filled with a clear liquid known as aqueous humor.

The ciliary body CB continuously forms aqueous humor in the posterior chamber PC by secretion from the blood vessels. The aqueous humor flows around the lens L and iris I into the anterior chamber and exits the eye through the trabecular meshwork TM, a sieve-like structure situated at the corner of the iris I and the wall of the eye (the corner is known as the iridocorneal angle). Some of the aqueous humor filters through the trabecular meshwork near the iris root into Schlemm's canal, a small channel that drains into the ocular veins. A smaller portion rejoins the venous circulation after passing through the ciliary body and eventually through the sclera (the uveoscleral route).

Glaucoma is a disease wherein the aqueous humor builds up within the eye. In a healthy eye, the ciliary processes secrete aqueous humor, which then passes through the angle between the cornea and the iris. Glaucoma appears to be the result of clogging in the trabecular meshwork. The clogging can be caused by the exfoliation of cells or other debris. When the aqueous humor does not drain properly from the clogged meshwork, it builds up and causes increased pressure in the eye, particularly on the blood vessels that lead to the optic nerve. The high pressure on the blood vessels can result in death of retinal ganglion cells and eventual blindness.

Closed angle (acute) glaucoma can occur in people who were born with a narrow angle between the iris and the cornea (the anterior chamber angle). This is more common in people who are farsighted (they see objects in the distance better than those which are close up). The iris can slip forward and suddenly close off the exit of aqueous humor, and a sudden increase in pressure within the eye follows.

Open angle (chronic) glaucoma is by far the most common type of glaucoma. In open angle glaucoma, the iris does not block the drainage angle as it does in acute glaucoma. Instead, the fluid outlet channels within the wall of the eye gradually narrow with time. The disease usually affects both eyes, and over a period of years the consistently elevated pressure slowly damages the optic nerve.

Implant

Figure 3:
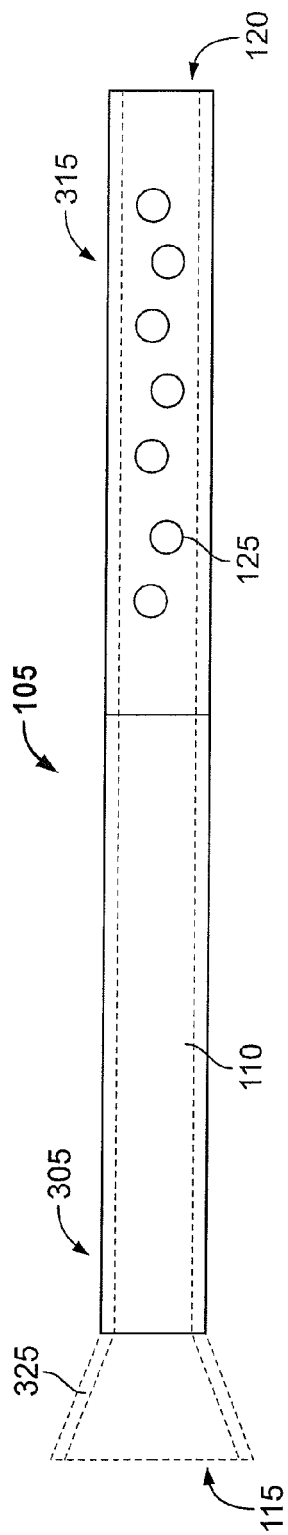
FIG. 3 shows an embodiment of an implant.

FIG. 3 shows a first embodiment of an implant 105. The implant 105 can be an elongate member having a proximal end, a distal end, and a structure that permits fluid (such as aqueous humor) to flow along the length of the implant such as through or around the implant from the anterior chamber to the suprachoroidal space. As mentioned above, the proximal end of the implant 105 is positioned in the anterior chamber and the distal end of the implant can extend to a region of the eye that is between the ciliary body and the sclera. The distal end of the implant can also extend to a region of the eye that is posterior to the ciliary body, such as between the choroid and the sclera. The suprachoroidal space can include the region between the sclera and the choroid as well as the region between the sclera and the ciliary body. The implant 105 can provide a fluid pathway for communication of aqueous humor between the anterior chamber and the suprachoroidal space.

In the embodiment of FIG. 3, the implant 105 can include at least one internal lumen 110 having at least one opening 115 for ingress of fluid (such as aqueous humor from the anterior chamber) and at least one opening 120 for egress of fluid into the suprachoroidal space. The implant 105 can include various arrangements of openings 125 that communicate with the lumen(s) 110. The openings 125 in the implant 105 can be filled with a material or mixture of materials, such as a sponge material, to prevent unwanted tissue in-growth into the openings 125 when the implant 105 is positioned in the eye. The sponge material can also be filled with a drug or other material that leaches into the eye over time upon implantation. During delivery of the implant 105, the openings 125 can be positioned so as to align with predetermined anatomical structures of the eye. For example, one or more openings 125 can align with the suprachoroidal space to permit the flow of aqueous humor into the suprachoroidal space, while another set of openings 125 can align with structures proximal to the suprachoroidal space, such as structures in the ciliary body or the anterior chamber of the eye.

The internal lumen 110 can serve as a passageway for the flow of aqueous humor through the implant 105 directly from the anterior chamber to the suprachoroidal space. In addition, the internal lumen 110 can be used to mount the implant 105 onto a delivery system, as described below. The internal lumen 110 can also be used as a pathway for flowing irrigation fluid into the eye generally for flushing or to maintain pressure in the anterior chamber. In the embodiment of FIG. 3, the implant 105 can have a substantially uniform diameter along its entire length, although the shape of the implant 105 can vary along its length (either before or after insertion of the implant). Moreover, the implant 105 can have various cross-sectional shapes (such as a, circular, oval or rectangular shape) and can vary in cross-sectional shape moving along its length. The cross-sectional shape can be selected to facilitate easy insertion into the eye.

FIG. 3 shows an embodiment of the implant 105 having a tubular or partially tubular structure. The implant 105 has a proximal region 305 and a distal region 315. In an embodiment, the proximal region 305 has a generally tubular shape with a collar 325. The collar 325 is shown in phantom lines to indicate that the collar 325 is optional. The collar 325 can be formed of the same material as the rest of the implant 105 or a different material. The collar 325 can have various shapes including a funnel shape such that the collar 325 provides a relatively wide opening that communicates with the internal lumen of the implant 105.

Figure 4:
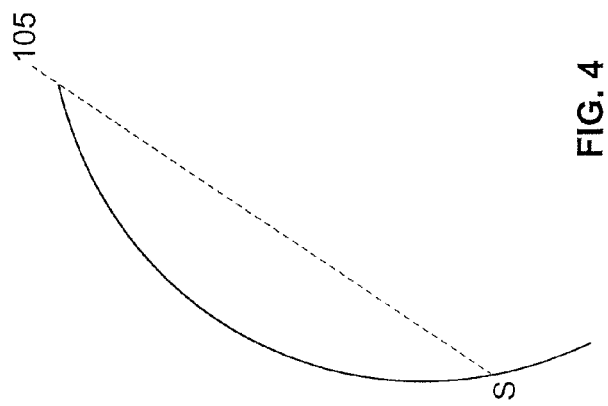
FIG. 4 shows relative shapes of the implant and the suprachoroidal space.

As illustrated schematically in FIG. 4, when implanted in the eye the implant 105 can form a dissection plane within or near the suprachoroidal space. The dissection plane can be straight or it can be curved as the dissection plane is being formed. At least a portion of the suprachoroidal space can be described as the space between two curved shells: a first, outer shell including the scleral tissue and a second, inner shell including the choroidal tissue. Alternatively, the first, outer shell can include the scleral tissue and the second, inner shell can include the ciliary body tissue. The shells can abut one another in that the inner surface of the sclera abuts the outer surface of the choroid (or ciliary body) with the suprachoroidal space being a virtual space that exists when the sclera is separated from the choroid (or ciliary body). The sclera has a tougher texture than the choroid or ciliary body. The implant 105 can have a stiffness such that its presence in or near the suprachoroidal space can increase or decrease ratios of curvature of one or both of the shells by pushing against the tough outer shell and/or the fragile inner shell. If the dissection plane is curved, the dissection plane can have a curvature that will follow a dissecting wire that performs the dissection or that is governed by the shape and/or stiffness of the implant positioned in the dissection plane. The curvature can be different from the curvature of the suprachoroidal space when the implant is implanted in the eye. Thus, the implant can form a straight or curved chord relative to the natural curvature of the suprachoroidal space if the implant were not present in the suprachoroidal space.

FIG. 4 shows a curve S (in solid line) that represents the natural curvature of the suprachoroidal space when the implant is not present. The implant 105 (represented by a dashed line) can be a straight implant (as shown in FIG. 4) or a curved implant that intersects the natural curvature S but does not conform to the natural curvature when implanted. The implant 105 can have a relative stiffness such that, when implanted, the implant 105 can deform at least a portion of the tissue adjacent the suprachoroidal space to take on a shape that is different than the natural curvature. In this manner, the implant 105 can form a tent or volume between the tissue boundaries (formed by the sclera and choroid) of the suprachoroidal space that does not exist naturally.

The implant 105 can have structural properties that cause the implant to interfere with and/or resist the natural curvature of the suprachoroidal space when implanted in the eye. In this regard, the implant 105 can have an effective or extrinsic Young's modulus (relative to the Young's modulus of the tissue boundary of the suprachoroidal space) that causes the implant to interfere with and locally change the curvature of the boundary between the sclera and the choroid when implanted in the eye. The effective modulus of the implant can depend upon the intrinsic modulus (or Young's modulus in this case), the shape and thickness of the implant. As mentioned above, the implant 105, when implanted, does not necessarily extend into a region of the suprachoroidal space that is between the sclera and the choroid. The implant can be positioned between the ciliary body and the sclera (within the supraciliary space) but still communicate with the suprachoroidal space. The implant 105 can be made of a material that has the requisite stiffness, or the implant can have structural properties, such as thickness or length, that achieve the requisite stiffness and deformation of the normal curvature of the sclera-suprachoroid boundary.

In an embodiment, a portion of the implant can be made of a material that has a Young's modulus that is less than 3,000 pounds per square inch (PSI). In another embodiment, the Young's modulus is greater than 30,000 psi. In another embodiment, the Young's modulus is between 30,000 psi and 70,000 psi. In another embodiment, the Young's modulus is 70,000 psi to 200,000 psi. In another embodiment, the Young's modulus is in the range of 100,000 psi to 200,000 psi. In another embodiment, the Young's modulus is approximately 200,000 psi. In another embodiment, the Young's modulus is less than or equal to 40,000,000 psi. It should be appreciated that the aforementioned values are exemplary and non-limiting. As mentioned above, the effective modulus of the implant depends upon intrinsic modulus (or Young's modulus in this case), shape and thickness of the implant. Therefore, if the modulus of the implant is below 30,000 psi, the dimensions of the implant such as material shape and thickness can be sufficient to maintain the effective modulus of the implant in order to overcome the bending modulus of one or more of the surrounding tissues.

In an embodiment, the implant 105 can have a column strength sufficient to permit the implant 105 to be inserted into suprachoroidal space such that the distal tip of the implant 105 tunnels through the eye tissue (such as the ciliary body) without structural collapse or structural degradation of the implant 105. In addition, the surface of the inner lumen can be sufficiently smooth relative to the delivery device (described in detail below) to permit the implant 105 to slide off of the delivery device during the delivery process. In an embodiment, the column strength can be sufficient to permit the implant to tunnel through the eye tissue into the suprachoroidal space without any structural support from an additional structure such as a delivery device.

The implant 105 can be made of various materials, including, for example, polyimide, Nitinol, platinum, stainless steel, molybdenum, or any other suitable polymer, metal, metal alloy, or ceramic biocompatible material or combinations thereof. Other materials of manufacture or materials with which the shunt can be coated or manufactured entirely include Silicone, PTFE, ePTFE, differential fluoropolymer, FEP, FEP laminated into nodes of ePTFE, silver coatings (such as via a CVD process), gold, prolene/polyolefins, polypropylene, poly(methyl methacrylate) (PMMA), acrylic, PolyEthylene Terephthalate (PET), Polyethylene (PE), PLLA, and parylene. The implant 105 can be reinforced with polymer, Nitinol, or stainless steel braid or coiling or can be a co-extruded or laminated tube with one or more materials that provide acceptable flexibility and hoop strength for adequate lumen support and drainage through the lumen. The shunt can alternately be manufactured of nylon (polyamide), PEEK, polysulfone, polyamideimides (PAI), polyether block amides (Pebax), polyurethanes, thermoplastic elastomers (Kraton, etc), and liquid crystal polymers.

Any of the embodiments of the implant 105 described herein can be coated on its inner or outer surface with one or more drugs or other materials, wherein the drug or material maintains the patency of the lumen or encourages in-growth of tissue to assist with retention of the implant within the eye or to prevent leakage around the implant. The drug can also be used for disease treatment. The implant can also be coated on its inner or outer surface with a therapeutic agent, such as a steroid, an antibiotic, an anti-inflammatory agent, an anticoagulant, an anti-glaucomatous agent, an anti-proliferative, or any combination thereof. The drug or therapeutic agent can be applied in a number of ways as is known in the art. Also the drug can be embedded in another polymer (nonabsorbable or bioabsorbable) that is coated on the implant.

The implant can also be coated or layered with a material that expands outward once the shunt has been placed in the eye. The expanded material fills any voids that are positioned around the shunt. Such materials include, for example, hydrogels, foams, lyophilized collagen, or any material that gels, swells, or otherwise expands upon contact with body fluids.

The implant can also be covered or coated with a material (such as polyester, ePTFE (also known as GORE-TEX.RTM.), PTFE that provides a surface to promote healing of the shunt into the surrounding tissue. In order to maintain a low profile, well-known sputtering techniques can be employed to coat the shunt. Such a low profile coating would accomplish a possible goal of preventing migration while still allowing easy removal if desired.

In an embodiment, the implant can have an inner diameter in the range of about 0.002" to about 0.050", an outer diameter in the range of about 0.006" to about 0.100", and a length in the range of about 0.100" to about 1.50". In another embodiment, the implant has an inner diameter in the range of about 0.008" to about 0.025". In another embodiment, the implant has an inner diameter in the range of about 0.010" to about 0.012". In another embodiment, the implant has an outer diameter in the range of about 0.012" to about 0.075". In another embodiment, the implant has an outer diameter in the range of about 0.025" to about 0.050". In another embodiment, the implant has a length in the range of about 0.125" to about 0.75". In another embodiment, the implant has a length in the range of about 0.25" to about 0.50". In another embodiment, the implant has an inner diameter of about 0.012", an outer diameter of about 0.020" and a length of about 0.25".

The implant can also have visual markers along its length to assist the user in positioning the desired portion of the implant within the anterior chamber. Further, the implant 105 and/or delivery system can employ alignment marks, tabs, slots or other features that allow the user to know alignment of the implant with respect to the delivery device. The implant 105 can include one or more features that aid in properly positioning the implant 105 in the eye. For example, the implant can have one or more visual, tomographic, echogenic, or radiopaque markers that can be used to aid in placement using any of the devices referenced above tuned to its applicable marker system. In using the markers to properly place the implant, the implant is inserted in the suprachoroidal space, until the marker is aligned with a relevant anatomic structure, for example, visually identifying a marker on the anterior chamber portion of the implant that aligns with the trabecular meshwork, or scleral spur, such that an appropriate length of the implant remains in the anterior chamber. Under ultrasound, an echogenic marker can signal the placement of the device within the suprachoroidal space. Any marker can be placed anywhere on the device to provide sensory feedback to the user on real-time placement, confirmation of placement or during patient follow up. Other structural features are described below.

Implant Delivery System

Figure 5A:
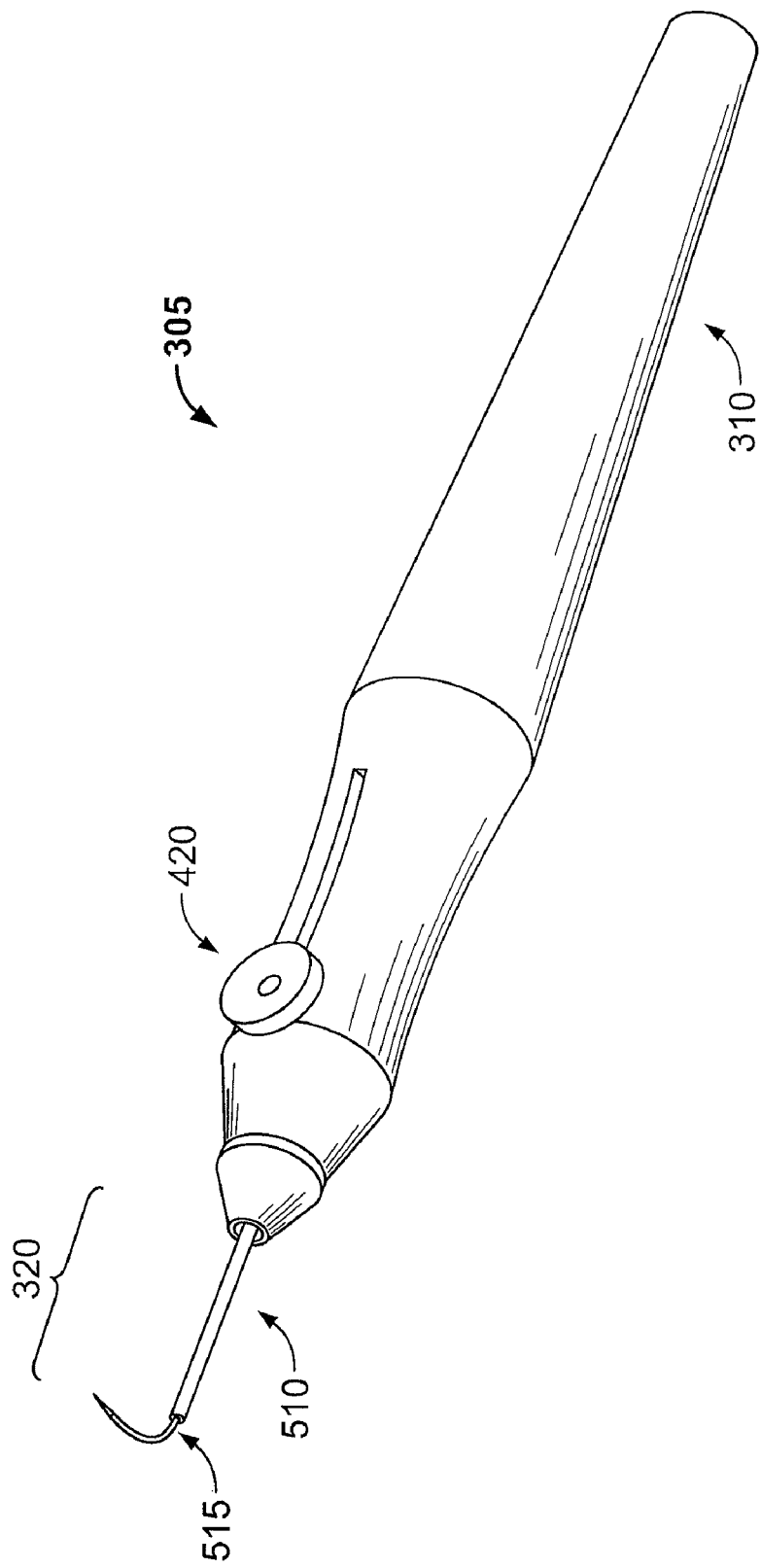
FIG. 5A shows an exemplary delivery system that can be used to deliver the implant into the eye.
Figure 5B:
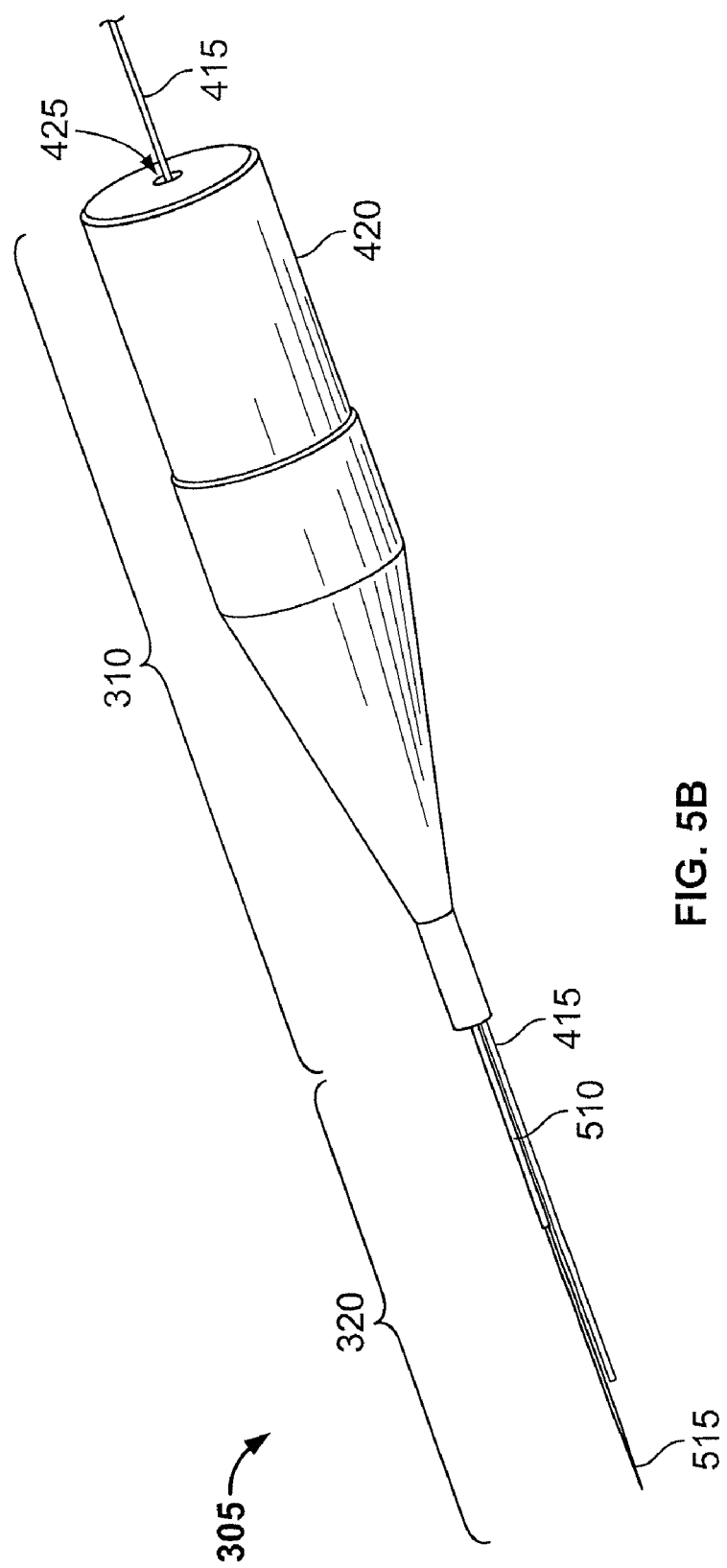
FIG. 5B shows another embodiment of a delivery system that can be used to deliver an implant into the eye.

In an embodiment, a delivery system is used to deliver an implant 105 into the eye such that the implant 105 provides fluid communication between the anterior chamber and the suprachoroidal space. FIG. 5A shows an embodiment of a delivery system 305 that can be used to deliver the implant 105 into the eye. FIG. 5B shows another embodiment of a delivery system 305 that can be used to deliver the implant 105 into the eye. It should be appreciated that these delivery systems 305 are for illustration and that variations in the structure, shape and actuation of the delivery system 305 are possible.

The delivery system 305 generally includes a proximal handle component 310 and a distal delivery component 320. The proximal handle component 310 can include an actuator 420 to control the release of an implant from the delivery component 320 into the target location in the eye. The proximal handle component 310 also can include a channel 425 for insertion of an internal visualization system, such as a fiber optic image bundle 415, as in the embodiment of FIG. 5B. Such a delivery system having an internal visualization system need not be used in conjunction with a gonioscope or viewing lens.

The delivery component 320 includes an elongate applier 515 that can insert longitudinally through the internal lumen of the implant 105 and a sheath 510 that can be positioned axially over the applier 515. The sheath 510 aids in the release of the implant 105 from the delivery component 320 into the target location in the eye. As best shown in FIGS. 5C and 5D, the actuator 420 can be used to control the applier 515 and/or the sheath 510. For example, the sheath 510 can be urged in a distal direction relative to the applier 515 to push the implant 105 off the distal end of the applier 515. Alternately, the sheath 510 can be fixed relative to the handle component 310. In this embodiment, the sheath 510 can act as a stopper that impedes the implant 105 from moving in a proximal direction as the applier 515 is withdrawn proximally from the implant 105 upon actuation of the actuator 420. In a first state shown in FIG. 5C, the applier 515 can be extended distally relative to the sheath 310. Movement of the actuator 420, such as in the proximal direction, can cause the applier 515 to slide proximally into the sheath 510 as shown in FIG. 5D. This effectively pushes the implant 105 off the distal end of the applier 515 and releases the implant 105 in a controlled fashion such that the target positioning of the implant 105 within the suprachoroidal space is maintained. The delivery device 305 can also incorporate a delivery channel within which the implant 105 can reside and a pusher that can push the implant out from the delivery channel during implantation.

Internal Implant Retention Layer

The outer diameter of the applier 515 is generally smaller than the inner diameter of the implant 105 (i.e. the fluid channel) such that the implant 105 can be loaded onto the applier 515. In some instances, the outer diameter of the applier 515 can be significantly smaller thereby creating a gap G between the applier 515 and the implant 105 (see FIG. 6E). This gap G leaves room for adding a retention layer 512 or a retention coating to the delivery component 320 (see FIG. 6F). The retention layer 512 can retain the implant 105 on the applier 515 during blunt dissection and implantation to prevent the implant 105 from inadvertently falling off the applier 515 until it is delivered to the desired target location within the eye. An advantage of a retention layer 512 between the implant and the applier is the very low profile of the delivery system 305 and a user's improved ability to visualize each step of implantation. Retention layers added externally around the implant, in contrast, significantly increase the profile of the delivery device and negatively impact the user's ability to visualize the steps of delivery. External retention layers can also increase the size of the incision needed to insert the delivery device.

FIGS. 6A-6D show cross-sectional schematic views of an implant 105 mounted on a delivery portion 320 inserted from the anterior chamber into the suprachoroidal space. The figures show an implant 105 mounted on the end of an applier 515, a sheath 510 sized and shaped to receive or abut a portion of the proximal end 125 of the implant 105, and a retention layer 512 providing an interference fit between the implant 105 and the applier 515. In this embodiment upon actuation the applier 515 slides in the proximal direction (arrow P) into the sheath 510. The proximal end 125 of the implant 105 abuts the distal edge of the sheath 510 to prevent the implant 105 from sliding in the proximal direction. This effectively pushes the implant 105 off the distal end of the applier 515 and controllably releases the implant 105 into the suprachoroidal space SC. The retention layer 512 moves with the applier 515 such that the applier 515 and retention layer 512 are fully withdrawn into the sheath 510. It should be appreciated that the sheath 510 can also advanced distally over the applier 515 upon actuation to deliver the implant 105 into the suprachoroidal space.

The retention layer 512 can include, for example, a sleeve such as a shrink-to-fit tube that can be inserted over the applier 515. The retention layer 512 can also be inserted through the fluid pathway of the implant 105. The retention layer 512 can also include a coating of material, for example on the outer diameter of the applier 515 or on the inner diameter of the implant 105. The retention layer 512 can also serve to prevent tissue from jamming into the gap G between the applier 515 and implant 105, for example during insertion of the device through the iris root or the ciliary body.

The retention layer 512 can be a variety of materials. In an embodiment, the retention layer 512 can be a generally soft, elastomeric, compliant polymer. For example, the material of the retention layer 512 can include silicone, thermoplastic elastomers (HYTREL, RATON, PEBAX), certain polyolefin or polyolefin blends, elastomeric alloys, polyurethanes, thermoplastic copolyester, polyether block amides, polyamides (such as Nylon), block copolymer polyurethanes (such as LYCRA). Some other exemplary materials include fluoropolymer (such as FEP and PVDF), FEP laminated into nodes of ePTFE, acrylic, low glass transition temperature acrylics, and hydrogels. It should also be appreciated that stiffer polymers can be made to be more compliant by incorporating air or void volumes into their bulk, for example, PTFE and expanded PTFE.

Dissection Dynamics of Applier

As described above, the delivery component 320 can include an elongate applier 515. The shape, structure, materials and material properties of the applier 515 are selected to optimize the gentle, blunt dissection between the tissue boundaries adjacent to the inner wall of the sclera and formation of the suprachoroidal space. The applier 515 can have a cross-sectional size and shape that complements the cross-sectional shape of the internal lumen of the implant 105 through which the applier 515 extends when the implant 105 is loaded thereon.

A variety of parameters including the shape, material, material properties, diameter, flexibility, compliance, pre-curvature and tip shape of the applier 515 can impact the performance of the applier 515 during gentle, blunt tissue dissection. The applier 515 desirably penetrates certain tissues while avoids penetration of other tissues. For example, it is desirable that the applier 515 be capable of penetrating the iris root or the ciliary body. The same applier 515 would beneficially be incapable of penetrating the scleral spur or inner wall of the sclera such that it can gently dissect between the tissue boundaries adjacent to the inner wall of the sclera.

The shape of the applier 515 along its long axis can be straight (as shown in FIG. 5B) or it can be can be curved along all or a portion of its length (as shown in FIG. 5A) in order to facilitate proper placement. In the case of the curved applier 515, the radius of curvature can vary. For example, the applier 515 can have a radius of curvature of 3 mm to 50 mm and the curve can cover from 0 degrees to 180 degrees. In one embodiment, the applier 515 has a radius of curvature that corresponds to or complements the radius of curvature of a region of the eye, such as the inner wall of the sclera. For example, the radius of curvature can be approximately 11-12 mm. Moreover, the radius of curvature can vary moving along the length of the applier 515. There can also be means to vary the radius of curvature of portions of the applier 515 during placement.

The distal tip shape of the applier 515 can play a part in whether or not the applier 515 penetrates certain tissues. For example, the scleral wall is a tougher tissue than the ciliary body or the iris root and generally requires a sharp tipped applier in order to be penetrated. The distal tip of the applier 515 can be sharp enough to penetrate the iris root or the ciliary body, but not so sharp (or sufficiently dull) so as not to easily penetrate the inner wall of the sclera. The tip shape of the applier 515 can vary. The distal tip of the applier 515 described herein can have a broad angle tip. The tip shape can be symmetrical relative to a central, longitudinal axis of the applier, such as a hemispheric tip, blunt-tipped cone, rounded-off cone tip. The tip shape can also be asymmetrical such as a shovel or spade shape tip. In an embodiment the applier 515 has a blunt tip. The blunt or atraumatic tip shape aids in the gentle dissection between tissues, such as the sclera and the ciliary body and the sclera and the choroid.

The distal tip of the applier 515 can also be coated to reduce friction during dissection. In an embodiment, the distal tip of the applier 515 is coated with a hydrophilic coating such as HYDAK (Biocoat, Horsham, Pa.) or another slippery coating as is known in the art. A balance can be struck between the angle of the distal tip, the angle of approach to the dissection entry point and whether or not the tip is covered by a slippery coating such that the risk of penetrating certain tissues (i.e. inner wall of the sclera) is reduced while the ability to penetrate other tissues (i.e. iris root or ciliary body) is maintained.

In addition to tip shape, coatings and pre-curvature of the applier 515, specific dissection performance also depends in part on the compliance and flexibility of the applier 515. The compliance and flexibility of the applier 515 is generally a function of the material, material properties and diameter of the material selected for the applier. As mentioned above, it is desirable to have an applier 515 that does not easily penetrate tissues such as the inner wall of the sclera. But it is also desirable to have an applier 515 that can penetrate through other tissues such as the iris root or the ciliary body. Similarly, it is desirable to have an applier 515 that can hug the curve of the inner scleral wall during blunt tissue dissection.

The outer diameter of the applier 515 can be selected and optimized based on the material and flexibility of the material used for the applier 515. An applier made of Nitinol, for example, can have an outer diameter of about 0.009 inches. Nitinol is a superelastic metal that is quite bendable yet is stiff enough to be pushed through the iris root and the ciliary body to reach to and hug the curve of the inner scleral wall during blunt dissection along the boundary between the sclera and the adjacent tissues to the inner scleral wall. When combined with other features of the applier, for example a blunt tip, a Nitinol applier having an outer diameter of about 0.009 inches can be used to gently dissect the tissue layers while avoiding tunneling or piercing one or both the inner scleral wall and choroid. Stainless steel spring wire is another material that could be used for the applier 515. Stainless steel wire is generally slightly stiffer than Nitinol. Thus, the outer diameter of an applier made of stainless steel wire may need to be somewhat smaller than the outer diameter for an applier made of Nitinol in order to achieve the same performance during blunt dissection. In an embodiment, the applier has an outer diameter of about 0.017 inches. It should be appreciated that for a given material's flexibility, the optimum outer diameter of the applier can be determined and extrapolated for an applier of a different material having a different degree of flexibility. Other materials considered for the applier 515 include compliant flexible wires made from a polymer or a polymer composite wire reinforced with high-strength fibers.

Methods of Implant Delivery

A method of delivering and implanting the implant into the eye is now described. In general, one or more implants 105 can be slidably mounted on and implanted in or near the suprachoroidal space using a delivery system as described herein. The mounting of the implant on the applier of the delivery system can be aided by a retention layer (or a retention coating on the applier or the internal walls of the implant) that reversibly retains the implant on the tip of the applier while still maintaining a flexible and low profile applier as described above. A retention layer can be used to avoid the implant from falling off the applier inadvertently during delivery until the user actuates the delivery component and effects controlled release of the implant from the applier 515, for example, upon proximal withdrawal of the applier 515. The implant 105 is then secured in the eye so that it provides fluid communication between the anterior chamber and the suprachoroidal space.

Implantation can be performed using a viewing lens as shown in FIG. 6G. A viewing lens 1405 (such as a gonioscopy lens represented schematically in FIG. 6G) is positioned adjacent the cornea. The viewing lens 1405 enables viewing of internal regions of the eye, such as the scleral spur and scleral junction, from a location in front of the eye. The viewing lens 1405 can optionally include one or more guide channels 1410 that are sized to receive the delivery portion 320 of the delivery system 305. It should be appreciated that the locations and orientations of the guide channels 1410 in FIG. 6G are merely for illustration and that the actual locations and orientations can vary depending on the angle and location where the implant 105 is to be delivered. An operator can use the viewing lens 1405 during delivery of the implant into the eye. The viewing lens 1405 can have a shape or cutout that permits the surgeon to use the viewing lens 1405 in a manner that does not cover or impede access to the corneal incision. Further, the viewing lens 1405 can act as a guide through which a delivery system 305 can be placed to predetermine the path of the device as it is inserted through the cornea.

An endoscope can also be used during delivery to aid in visualization. For example, a twenty-one to twenty-five gauge endoscope can be coupled to the implant during delivery such as by mounting the endoscope along the side of the implant or by mounting the endoscope coaxially within the implant. Ultrasonic guidance can be used as well using high resolution bio-microscopy, OCT and the like. Alternatively, a small endoscope can be inserted though another limbal incision in the eye to image the tissue during the procedure.

Each step of implantation can also be visualized using an internal visualization system (see for example U.S. patent application Ser. No. 12/492,085). Visualization can occur continuously during implantation or other procedures without the need for re-positioning or removing one or more components of the imaging systems and without the need for viewing through a goniolens.

Figure 7:
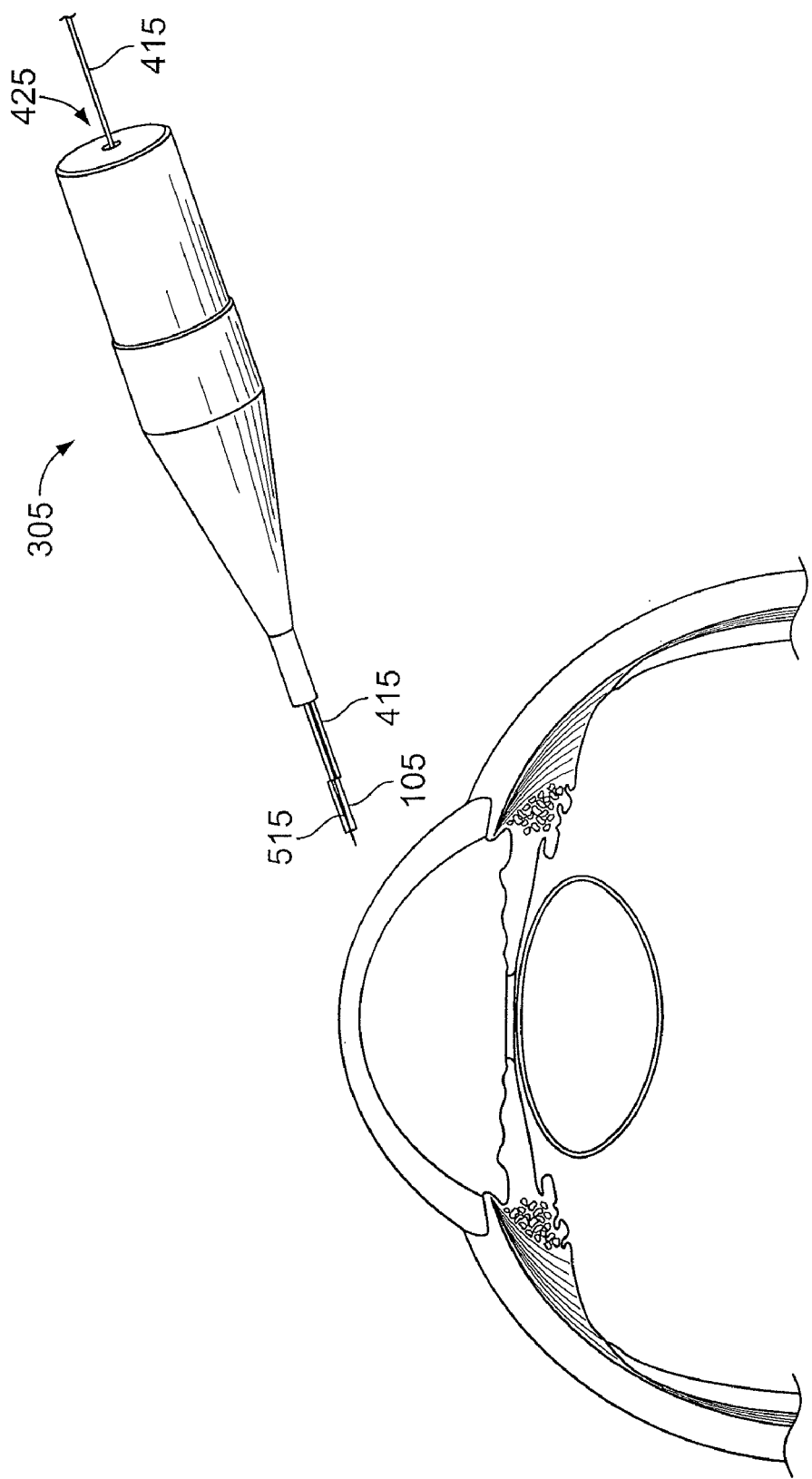
FIG. 7 shows a schematic of the fiber optic visualization and delivery system positioned for penetration into the eye.

With reference to FIG. 7, the delivery portion 320 is positioned such that the distal tip of the applier 515 and the implant 105 penetrate through a small, corneal incision to access the anterior chamber. In this regard, the single incision can be made in the eye, such as within the limbus of the cornea. In an embodiment, the incision is very close to the limbus, such as either at the level of the limbus or within 2 mm of the limbus in the clear cornea. The applier 515 can be used to make the incision or a separate cutting device can be used. For example, a knife-tipped device or diamond knife can be used to initially enter the cornea. A second device with a spatula tip can then be advanced over the knife tip wherein the plane of the spatula is positioned to coincide with the dissection plane.

The corneal incision can have a size that is sufficient to permit passage of the implant 105 on the applier 515 there through. In an embodiment, the incision is about 1 mm in size. In another embodiment, the incision is no greater than about 2.85 mm in size. In another embodiment, the incision is no greater than about 2.85 mm and is greater than about 1.5 mm. It has been observed that an incision of up to 2.85 mm is a self-sealing incision. For clarity of illustration, the FIG. 7 is not to scale.

After insertion through the incision, the applier 515 can be advanced into the anterior chamber along a pathway that enables the implant 105 to be delivered from the anterior chamber into the suprachoroidal space. With the applier 515 positioned for approach, the applier 515 can be advanced further into the eye such that the blunt distal tip of the applier 515 and/or the implant 105 penetrates the tissue at the angle of the eye, for example, the iris root or a region of the ciliary body or the iris root part of the ciliary body near its tissue border with the scleral spur, to be discussed in more detail below.

The scleral spur is an anatomic landmark on the wall of the angle of the eye. The scleral spur is above the level of the iris but below the level of the trabecular meshwork. In some eyes, the scleral spur can be masked by the lower band of the pigmented trabecular meshwork and be directly behind it. The applier can travel along a pathway that is toward the angle of the eye and the scleral spur such that the applier passes near the scleral spur on the way to the suprachoroidal space, but does not necessarily penetrate the scleral spur during delivery. Rather, the applier 515 can abut the scleral spur and move downward to dissect the tissue boundary between the sclera and the ciliary body, the dissection entry point starting just below the scleral spur near the iris root IR or the iris root portion of the ciliary body. In another embodiment, the delivery pathway of the implant intersects the scleral spur.

The applier 515 can approach the angle of the eye from the same side of the anterior chamber as the deployment location such that the applier 515 does not have to be advanced across the iris. Alternately, the applier 515 can approach the angle of the eye from across the anterior chamber AC such that the applier 515 is advanced across the iris and/or the anterior chamber toward the opposite angle of the eye. The applier 515 can approach the angle of the eye along a variety of pathways. The applier 515 does not necessarily cross over the eye and does not intersect the center axis of the eye. In other words, the corneal incision and the location where the implant is implanted at the angle of the eye can be in the same quadrant when viewed looking toward the eye along the optical axis. Also, the pathway of the implant from the corneal incision to the angle of the eye ought not to pass through the centerline of the eye to avoid interfering with the pupil.

Figure 8:
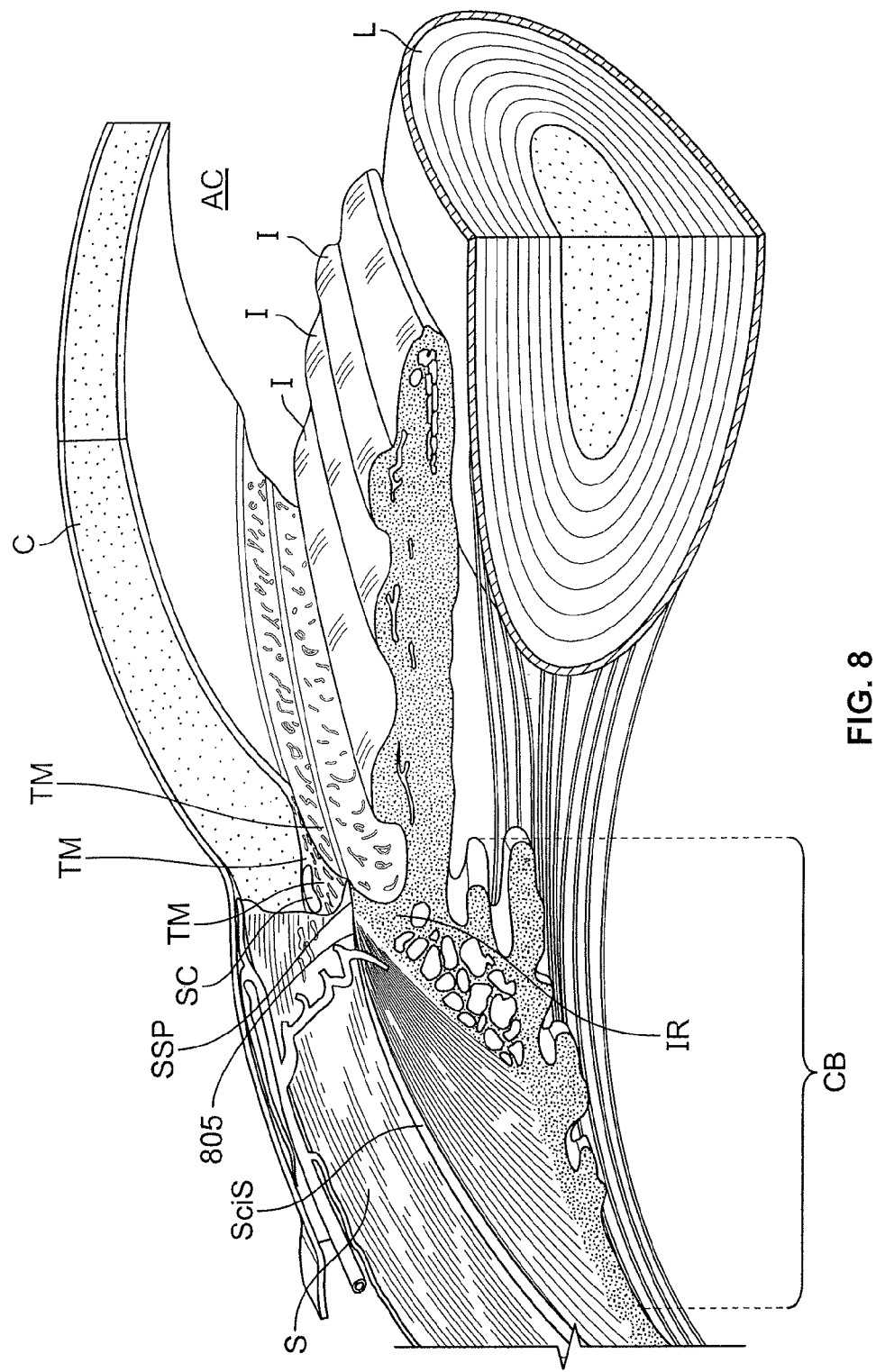
FIG. 8 shows an enlarged view of a portion of the anterior region of the eye in cross-section.

FIG. 8 shows an enlarged view of the anterior region of the eye showing the anterior chamber AC, the cornea C, the iris I, and the sclera S. An implant 105 mounted on an applier 515 can approach the angle of the eye from the anterior chamber AC. As mentioned above, the applier 515 moves along a pathway such that the dissection entry point of the distal tip of the applier 515 can penetrate the iris root IR or the iris root portion of the ciliary body CB near the scleral spur SSp. Other penetration points near the angle of the eye are also considered herein. The surgeon can rotate or reposition the handle of the delivery device in order to obtain a proper approach trajectory for the applier 515, as described in further detail below.

The applier 515 with the implant 105 positioned thereupon can be advanced through tissues near the angle of the eye, such as the iris root IR, the ciliary body or the iris root portion of the ciliary body. As the applier 515 is advanced it can penetrate an area of fibrous attachment 805 between the scleral spur and the ciliary body. This area of fibrous attachment 805 can be approximately 1 mm in length. Once the distal tip of the applier 515 is urged past this fibrous attachment region 805, it then can more easily cause the sclera S to peel away or otherwise separate from the ciliary body and choroid as it follows the inner curve of the sclera A to form the suprachoroidal space SChS. As described above, a combination of the applier's tip shape, material, material properties, diameter, flexibility, compliance, coatings, pre-curvature etc. make it more inclined to follow an implantation pathway that mirrors the curvature of the inner wall of the sclera and between tissue layers such as the sclera S and choroid or the sclera and the ciliary body.

The applier 515 can be continuously advanced into the eye, for example approximately 6 mm. The dissection plane of the applier 515 can follow the curve of the inner scleral wall such that the implant 105 mounted on the applier 515, for example after penetrating the iris root IR or the iris root portion of the ciliary body CB, can bluntly dissect the boundary between tissue layers of the scleral spur SSp and the ciliary body CB such that a distal region of the implant 105 extends through the supraciliary space SCiS and then, further on, is positioned between the tissue boundaries of the sclera and the choroid forming the suprachoroidal space SChS.

Once properly positioned, the implant 105 can be released. The implant 105 can be released for example by withdrawing the applier 515 such that the implant 105 is effectively pushed in a controlled manner off the tip of the delivery portion 320 with the sheath 510 (for example via the manner described above with reference to FIGS. 6A-6D). A retention layer 512 can optionally be used to assist in retaining the implant 105 on the applier 515 during the steps of delivery. However, the relationship between the retention layer 512 and the implant 105 is readily reversible such that the applier 515 and retention layer 512 can be withdrawn into the sheath 510 to controllably release the implant 105 from the tip of the applier upon arrival at the target location within the eye.

Figure 9:
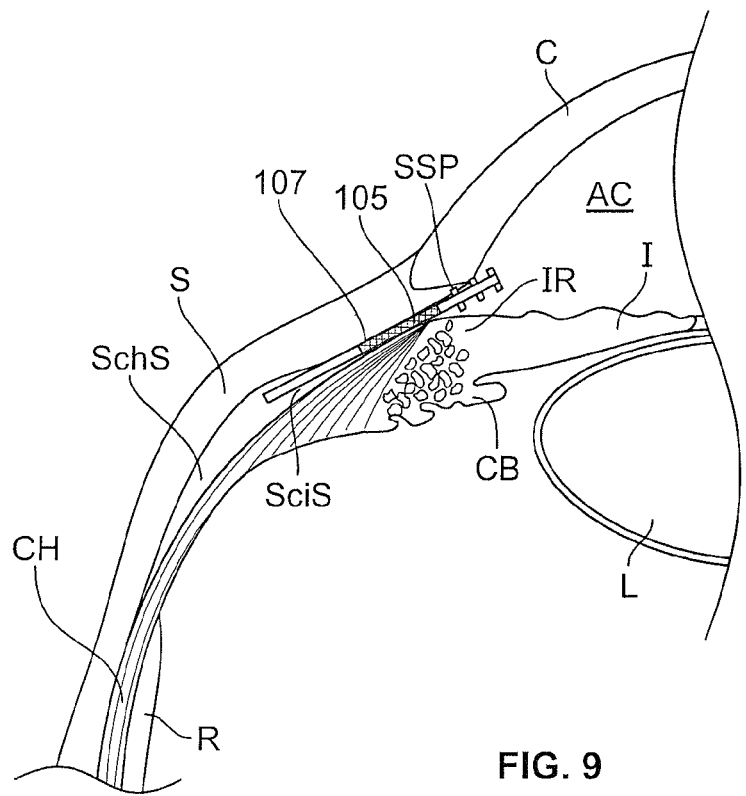
FIG. 9 shows the implant positioned within the suprachoroidal space.
Figure 10A:
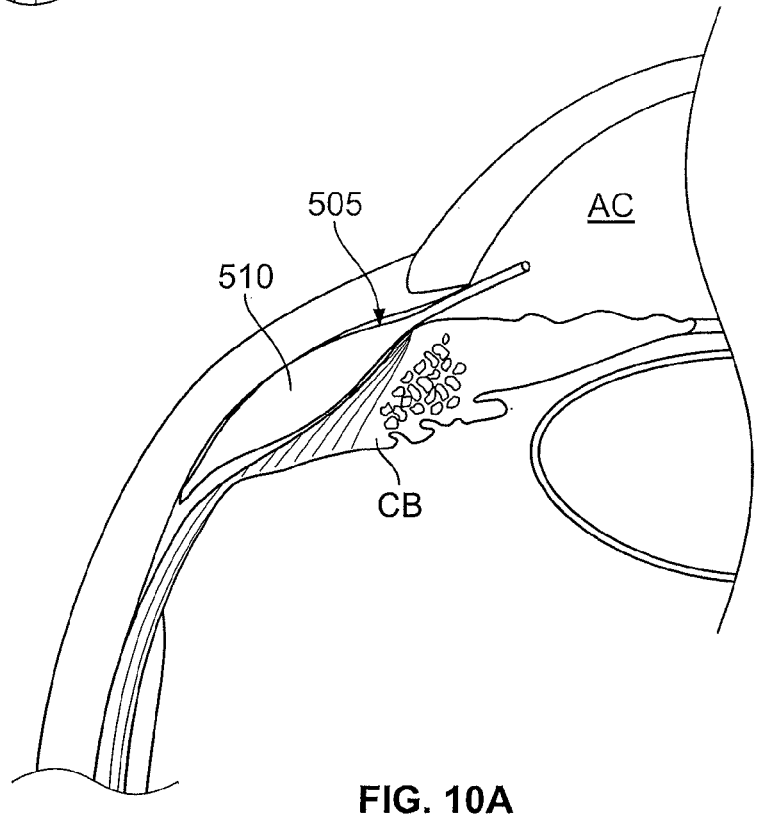
FIGS. 10A-10D show other implants that reduces aqueous humor production.
Figure 10B:
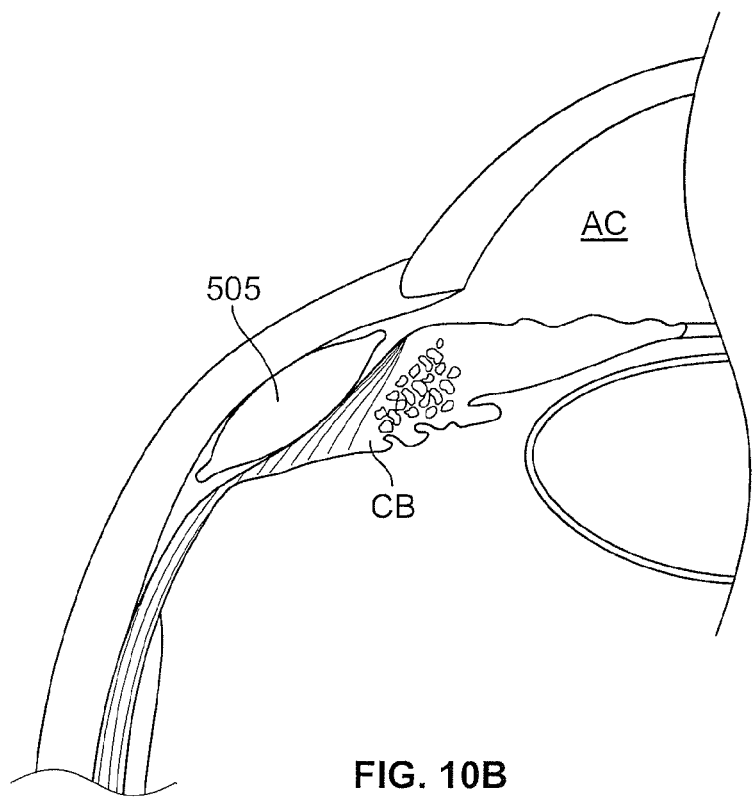
Figure 10C:
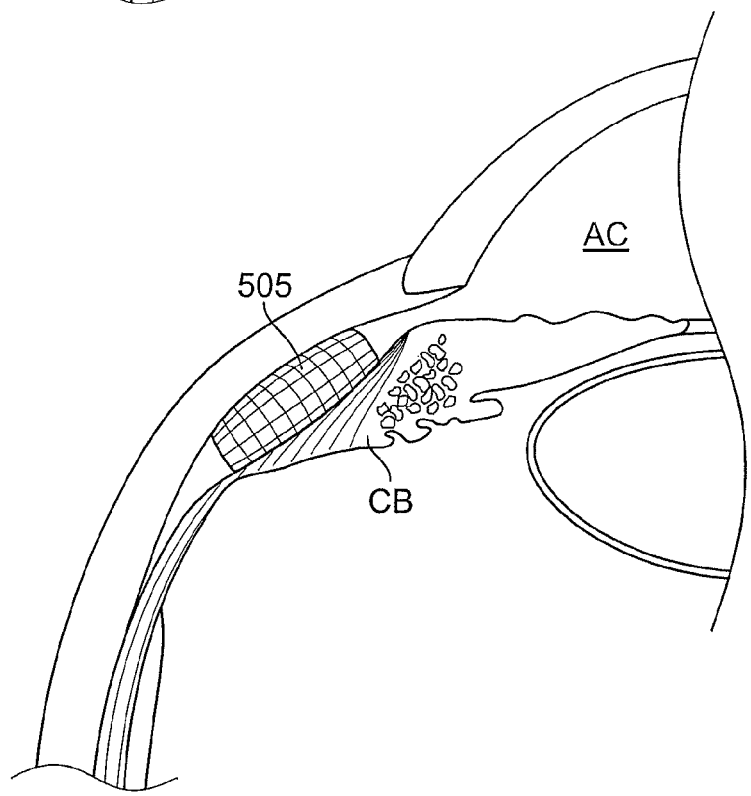
Figure 10D:
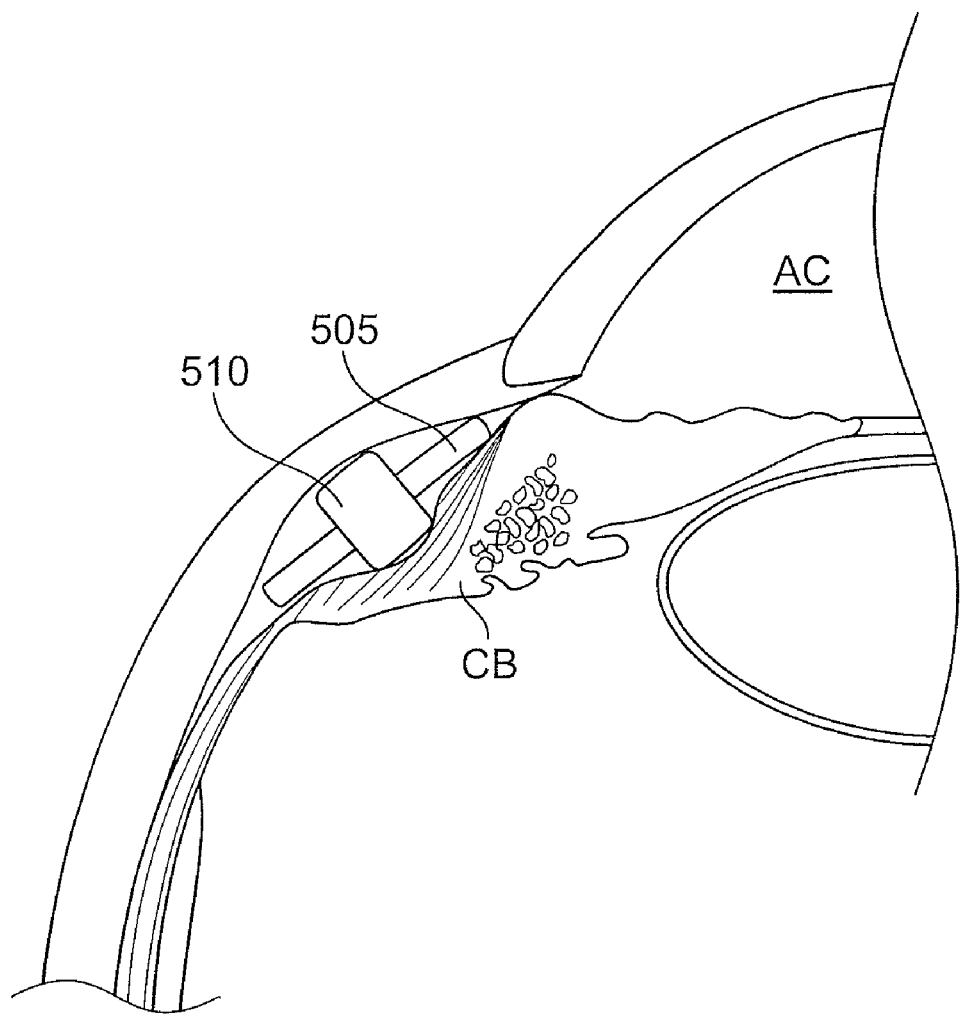

The implant 105 can include one or more structural features that aid to anchor or retain the implant 105 in the target region in the eye. The structural features can include flanges, protrusions, wings, tines, or prongs, and the like that can lodge into the surrounding eye anatomy to retain the implant 105 in place and prevent the implant 105 from moving further into the suprachoroidal space SChS. The structural features also provide regions for areas of fibrous attachment between the implant 105 and the surrounding eye anatomy. FIG. 9 illustrates schematically an approximately 1 mm circumferential band 107 of the implant 105 near the junction of the iris root and the scleral spur SSp along the inside of the scleral wall toward the back of the eye at which fibrous attachment can occur. Fibrous attachment can result, for example, from endothelial cell growth in, around and/or between retention features of the implant 105. In addition, a small amount of scaring in and around an area of fibrous tissue attachment between the scleral spur and the ciliary body in the region of the iris root portion of the ciliary body can provide for additional fixation to prop up the implant in its target location. A proximal portion of the implant 105 can remain within the anterior chamber AC. In one embodiment, at least 1 mm to 2 mm of the implant (along the length) remains in the anterior chamber.

The implant 105 can be positioned in the eye so that a portion of the implant is sitting on top of the ciliary body CB. The ciliary body CB can act as a platform off of which the implant 105 can cantilever into the suprachoroidal space SChS. The implant 105 can have a relative stiffness such that, when implanted, the implant 105 deforms at least a portion of the tissue adjacent the suprachoroidal space to take on a shape that is different than the natural curvature. In this manner, the implant 105 can lift or "tent" the sclera S outward such that the suprachoroidal space SChS is formed around the distal end of the implant 105. The tenting of the sclera S as shown in FIG. 9 has been exaggerated for clarity of illustration. It should be appreciated that the actual contour of the tented region of tissue may differ in the actual anatomy. Whether the distal end of the implant 105 is positioned between the sclera and the ciliary body or the sclera and the choroid, the implant 105 can act as a flow pathway between the anterior chamber AC and the suprachoroidal space SChS without blockage of the outflow pathway by surrounding tissues such as the sclera or the choroid.

The implant can also be positioned in the eye such that a portion of the implant exerts a force or pressure on or against the ciliary body. The implant can exert a displacing force against the ciliary body such that the implant interferes with and/or resists the natural curvature of the ciliary body. The implant can interfere with and locally change the curvature of the boundary between the sclera and at least a portion of the ciliary body when implanted in the eye. As mentioned previously, the ciliary body produces aqueous humor. The force exerted by the implant on the ciliary body can decrease production of aqueous humor from ciliary body. The stiff configuration of the implant 105 can push down or radially inward on the ciliary body In an embodiment, an implant 505 can be an elongate, stiff shunt having an internal lumen and an expanded and/or expandable region 510 (see, FIG. 10A-10D). The implant 505 can shunt aqueous from the anterior chamber to the suprachoroidal space. The expandable region 510 of the implant 505 can impart a pressure against the ciliary body CB such that aqueous production is reduced. The pressure can be in a downward direction or a radially inward direction on the ciliary body CB. In an embodiment, the pressure against the ciliary body CB causes at least a portion of the ciliary body CB to be displaced and aqueous production reduced. In another embodiment, the implant does not displace the ciliary body CB but simply exerts pressure against the ciliary body to reduce aqueous humor production. The combination of reduced aqueous production and the shunting of aqueous out of the anterior chamber can act in coordination to reduce pressure within the anterior chamber.

The implant 505 can be an elongated tubular member having a proximal end, a distal end, and a structure that permits flow of fluid (such as aqueous humor) along the length of the implant such as through or around the implant from the anterior chamber. For example, the implant 505 can have at least one internal lumen having at least one opening for ingress of fluid and at least one opening for egress of fluid. The implant 505 need not include an internal lumen that fluidically communicates with the anterior chamber AC. The implant 505 can be a solid bar that allows for flow of aqueous humor along an outside surface. The implant 505 can also permit no flow of aqueous humor through or around the implant and instead apply only a force on the ciliary body to reduce aqueous humor production.

The implant 505 can have a variety of shapes and configurations. The implant 505 can have a shape or take on a shape that optimizes the radial pressure exerted on the ciliary body CB. The implant 505 can be or include an inflatable balloon, expandable spacer or cage, or other configuration. The implant 505 can have one or more expandable regions of Hydrogel 510. The implant 505 can also have a variety of cross-sections and shapes. For example, the implant can have a circular, oval, rectangular or star shape and can vary in cross-sectional shape moving along its length. In an embodiment, the implant 505 can have a star or cross-shape such that aqueous from the anterior chamber flows through one or more convoluted outer surface of the implant.

The pressure exerted by the implant 505 on the ciliary body CB can vary. In an embodiment, the implant 505 exerts a radially-inward (relative to the center of the eye) force on the ciliary body CB. In another embodiment, the implant exerts a force that has a component that points radially inward and another component that does not point radially-inward.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

The invention claimed is:

1. A method of delivering an ocular implant into an eye, comprising:
   forming an incision in a cornea of the eye;
   using a delivery instrument to insert the ocular implant through the incision into the anterior chamber of the eye;
   passing the implant through the anterior chamber;
   positioning at least a portion of the implant within the supraciliary space between the ciliary body and the sclera so that the implant forms a flow pathway configured to drain aqueous humor from the anterior chamber toward the suprachoroidal space after release of the implant from the delivery instrument; and
   releasing the implant from the delivery instrument such that the implant transitions from a first shape to a straight shape after release of the implant from the delivery instrument.

2. The method of claim 1, wherein the straight shape after release of implant from the delivery instrument of the implant forms a chord relative to a curvature of the sclera of the eye.

3. The method of claim 1, wherein the implant is formed of a material having a stiffness greater than a stiffness of at least some eye tissue adjacent the implant when implanted in the eye.

4. The method of claim 1, wherein releasing the implant from the delivery instrument comprises withdrawing a portion of the delivery instrument out of the implant.

5. The method of claim 1, wherein as the implant transitions to the straight shape, the implant deforms at least some adjacent eye tissue so as to form a tented volume beneath the sclera.

6. The method of claim 5, wherein the distal end of the implant presses against the sclera and a portion of the implant presses against and deforms the ciliary body to form the tented volume.

7. The method of claim 1, further comprising loading the ocular implant onto the delivery instrument.

8. The method of claim 7, wherein loading the ocular implant onto the delivery instrument comprises inserting an elongated applier element of the delivery instrument into an internal lumen of the ocular implant, the applier element comprising an elongated body.

9. The method of claim 8, wherein a default state of the implant is straight, and wherein the implant transitions to a shape that conforms to a shape of the applier element when the applier element is inserted into the internal lumen of the implant.

10. The method of claim 1, wherein positioning at least a portion of the implant within the supraciliary space between the ciliary body and the sclera comprises positioning a proximal end of the implant in the anterior chamber and a distal end of the implant within the supraciliary space such that an internal lumen of the implant can drain aqueous humor from the anterior chamber toward the suprachoroidal space after release of the implant from the delivery instrument.

11. The method of claim 1, wherein the implant is straight along its entire length after release of the implant from the delivery instrument.

12. The method of claim 1, wherein the implant is cylindrical along its entire length.

13. A method of delivering an ocular implant into an eye, comprising:
   using a delivery instrument to insert the ocular implant into the anterior chamber of the eye;
   passing the implant through the anterior chamber;
   using the delivery instrument to form an opening in tissue adjacent the scleral spur and to separate a portion of a ciliary body from sclera;
   positioning at least a portion of the implant through the opening and between the sclera and ciliary body so that the implant forms a flow pathway configured to drain aqueous humor from the anterior chamber toward the suprachoroidal space after release of the implant from the delivery instrument; and
   releasing the implant from the delivery instrument such that the implant transitions from a first shape to a second shape that is less curved than the first shape after release of the implant from the delivery instrument.

14. The method of claim 13, wherein the first shape of the implant conforms to a shape of a distal portion of the delivery instrument when the implant is removably couple to the delivery instrument.

15. The method of claim 13, wherein the implant is straight when in the second shape.

16. The method of claim 13, wherein releasing the implant from the delivery instrument comprises withdrawing a portion of the delivery instrument out of the implant.

17. The method of claim 13, wherein as the implant transitions to the second shape, the implant deforms at least some adjacent eye tissue so as to form a tented volume beneath the sclera.

18. The method of claim 17, wherein the distal end of the implant presses against the sclera and a portion of the implant presses against and deforms the ciliary body to form the tented volume.

19. The method of claim 13, further comprising loading the ocular implant onto the delivery instrument.

20. The method of claim 19, wherein loading the ocular implant onto the delivery instrument comprises inserting an elongated applier element of the delivery instrument into an internal lumen of the ocular implant, the applier element comprising an elongated body.

21. The method of claim 13, further comprising forming an incision in a cornea of the eye, and passing the implant through the incision into the anterior chamber.

22. The method of claim 13, wherein an outlet of the implant is in the suprachoroidal space after the implant is released from the delivery instrument.

23. The method of claim 13, wherein an outlet of the implant is in the supraciliary space after the implant is released from the delivery instrument.

24. The method of claim 13, wherein a distal end of the implant is in the supraciliary space after the implant is released from the delivery instrument.

25. The method of claim 13, wherein the implant is straight along its entire length after release of the implant from the delivery instrument.

26. The method of claim 13, wherein the implant is cylindrical along its entire length.

* * * * *